US011148989B2

(12) United States Patent
Miyake et al.

(10) Patent No.: US 11,148,989 B2
(45) Date of Patent: Oct. 19, 2021

(54) DIALKOXYALKADIENYNE COMPOUND AND A PROCESS FOR PREPARING THE SAME AND A PROCESS FOR PREPARING A DIENYNAL COMPOUND

(71) Applicant: Shin-Etsu Chemical Co., Ltd., Tokyo (JP)

(72) Inventors: Yuki Miyake, Niigata (JP); Takeshi Kinsho, Niigata (JP); Ryo Komatsu, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/010,241

(22) Filed: Sep. 2, 2020

(65) Prior Publication Data

US 2021/0061744 A1 Mar. 4, 2021

(30) Foreign Application Priority Data

Sep. 4, 2019 (JP) .............................. JP2019-160884

(51) Int. Cl.
| | | |
|---|---|---|
| C07C 45/00 | (2006.01) | |
| C07C 41/26 | (2006.01) | |
| C07C 41/50 | (2006.01) | |
| C07C 45/51 | (2006.01) | |
| C07C 41/48 | (2006.01) | |
| C07C 43/303 | (2006.01) | |
| C07C 43/14 | (2006.01) | |
| C07C 47/20 | (2006.01) | |

(52) U.S. Cl.
CPC ............ *C07C 45/515* (2013.01); *C07C 41/26* (2013.01); *C07C 41/48* (2013.01); *C07C 41/50* (2013.01); *C07C 43/303* (2013.01); *C07C 43/14* (2013.01); *C07C 47/20* (2013.01)

(58) Field of Classification Search
CPC ........ C07C 45/515; C07C 41/26; C07C 41/50
See application file for complete search history.

(56) References Cited

PUBLICATIONS

Chelpanova et al. "Conjugated systems. CLVII. Synthesis and hydrobromination of 4-penten-2-ynal. Enyne compounds" Zhurnal Obshchei Khimii, vol. 32, 2487-2489. CA Abstract No. 58:72891; Accession No. 1963:72891 HCAPLUS (Year: 1962).
Extended European Search Report corresponding to European Patent Application No. 20194350.3 (5 pages) (dated Feb. 1, 2021).
Chelpanova et al. "Conjugated systems. CLVII. Synthesis and hydrobromination of 4-penten-2-ynal" Lensovet Leningrad Technological Institute, Translated from Zhurnal Obshchci Khimii, 12(8):2453-2455 (1962; Original article submitted Jul. 8, 1961).
Hoddle et al. "Synthesis and Field Evaluation of the Sex Pheromone of Stenoma catenifer (Lepidoptera: Elachistidae)" Journal of Economic Entomology, Ecology and Behavior, 102(4):1460-1467 (2009).
Jones et al. "Researches on Acetylenic Compounds. Part LX.* The Synthesis of Three Natural Polyacetylenic Hydrocarbons" Journal of the Chemical Society (Resumed), pp. 1054-1059 (1958).
Zou et al. "Improved synthesis of (9Z)-9, 13-tetradecadien-11-ynal, the sex pheromone of the avocado seed moth, Stenoma catenifer" Tetrahedron Letters, 51(9)1336-1337 (2010).
Millar et al. "(9Z)-9,13-Tetradecadien-11-ynal, the sex pheromone of the avocado seed moth, Stenoma catenifer" Tetrahedron Letters, 49(33):4820-4823 (2008).

*Primary Examiner* — Sikarl A Witherspoon
(74) *Attorney, Agent, or Firm* — Myers Bigel, P.A.

(57) ABSTRACT

A process for preparing a dienynal compound of the following general formula (2):

$$CH_2=CHC\equiv CCH=CH(CH_2)_nCHO \qquad (2),$$

wherein n represents an integer of 0 to 11, the process comprising a step of hydrolyzing a dialkoxyalkadienyne compound of the following general formula (1):

$$CH_2=CHC\equiv CCH=CH(CH_2)_nCH(OR^1)(OR^2) \qquad (1)$$

wherein $R^1$ and $R^2$ represent, independently of each other, a monovalent hydrocarbon group having 1 to 15 carbon atoms, preferably 1 to 8, more preferably 1 to 4, or $R^1$ and $R^2$ may be bonded to each other to form a divalent hydrocarbon group, $R^1$-$R^2$, having from 2 to 10 carbon atoms, and n represents an integer of 0 to 11, to obtain the dienynal compound (2).

$$CH_2=CHC\equiv CCH=CH(CH_2)_nCH(OR^1)(OR^2) \xrightarrow[\text{Water}]{\text{Acid}}$$
(1)
$$CH_2=CHC\equiv CCH=CH(CH_2)_nCHO$$
(2)

18 Claims, No Drawings

DIALKOXYALKADIENYNE COMPOUND AND A PROCESS FOR PREPARING THE SAME AND A PROCESS FOR PREPARING A DIENYNAL COMPOUND

TECHNICAL FIELD

The present invention relates to a dialkoxyalkadienyne compound and a process for preparing the dialkoxyalkadienyne compound and a process for preparing a dienynal compound.

BACKGROUND ART

Avocado seed moth (*Stenoma catenifer*) is a most serious pest to attack avocado fruit in the Central and South America such as Mexico, Guatemala, Peru, Ecuador, and Brazil. For instance, pesticides are sprayed 7 to 11 times in a season in some areas of the South America. Nevertheless, it is said that 60% of the fruits is damaged. One of the reasons for this is that larvae of this pest penetrate into the flesh, which makes the control with pesticides difficult. Accordingly, biological control is attracting attention, and use of a sex pheromone is thought to be promising.

A sex pheromone of *Stemoma catenifer* is a dienynal compound, (9Z)-9,13-tetradecadien-11-ynal (Non-Patent Literatures 1 and 2, listed below).

A method tor synthesizing this sex pheromone is reported where, for example, a starting material, 9-decyn-1-ol, is hydroborated with pinacolborane, followed by iodination, protection of a hydroxyl group by THP, coupling reaction with 2-propyn-1-ol in the presence of a palladium catalyst, oxidation of a hydroxyl group with manganese dioxide, introduction of a terminal olefinic structure by a Wittig reaction, elimination of the THP protecting group to obtain (9Z)-9,13-tetradecadien-11-yn-1-ol, whose hydroxyl group is then oxidized with pyridinium chlorochromate (PCC) to obtain (9Z)-9,13-tetradecadien-11-ynal (Non-patent Literature 1). It is also reported that an alkyne terminal of 2-(9-decyn-1-yloxy)tetrahydro-2H-pyran is deprotonated with n-butyl lithium, followed by iodination, hydroboration with dicyclohexylborane, protonation, coupling reaction with 1-buten-3-yne in the presence of a palladium catalyst, damnation of the THP protecting group to obtain (9Z)-9,13-tetradecadien-11-yn-1-ol, whose hydroxyl group is then oxidized with pyridinium chlorochromate (PCC) to obtain (9Z)-9,13-tetradecadien-11-ynal (Non-Patent Literatures 2 and 3, listed below).

LIST OF THE PRIOR ART

Non-Patent Literatures

[Non-Patent Literature 1] Jocelyn G. Millar et al, Tetrahedron Letters. 2008, 49: 4820-4823.
[Non-Patent Literature 2] Mark S. Hoddle et al, Ecology and Behavior. 2009, 102 (4): 1460-1467.
[Non-Patent Literature 3] Jocelyn G. Millar et al, Tetrahedron Letters. 2010, 51:1336-1337.

SUMMARY OF THE INVENTION

The synthetic method reported in Non-Patent Literature 1 uses expensive pinacolborane and palladium catalyst, hi addition, manganese dioxide and a chromium compound, PCC, used in the oxidation in Non-Patent Literature 1 cause a large environmental load. Further, the oxidation reaction often involves a danger of explosion. Accordingly, practice of the method in an industrial scale is difficult. A yield is so extremely low as 7%.

The synthetic methods reported in Non-Patent Literatures 2 and 3 use l-buten-3-yne, which is difficult to industrially obtain, and an expensive palladium catalyst hi addition, a chromium compound, PCC, used in the oxidation in Non-Patent Literature 1 causes a large environmental load. Further, the oxidation reaction often involves a danger of explosion. Accordingly, practice of the method in an industrial scale is difficult. An overall yield is so extremely low as 25%.

Furthermore, the synthetic methods reported in Non-Patent Literatures 1, 2 and 3 involve (9Z)-9,13-tetradecadien-11-yn-1-ol as an intermediate. This alcohol is known to decrease attractiveness for *Stemoma catenifer*. Accordingly, it is preferable that the synthesized (9Z)-9,13-tetradecadien-11-ynal is not contaminated with this alcohol. Therefore, it is desirable not to use the alcohol as an intermediate or a precursor (Non-Patent Literature 2).

The present invention has been made in the aforesaid circumstances, and provides a dialkoxyalkadienyne compound useful as an intermediate, a process for producing the same, and a process for producing a dienynal compound from this intermediate.

As a result of the intensive researches, the present inventors have found dial a dialkoxyalkadienyne compound is useful as an intermediate for preparing a dienynal compound, and that a dienynal compound may be prepared from the dialkoxyalkadienyne compound in a short process and in a high yield without contamination with a dienynol compound which is an attraction inhibitor, such as the aforesaid (9Z)-9,13-tetradecadien-11-yn-1-ol, and thus have completed the present invention.

According to one aspect of the present invention, there is provided a process for preparing a dienynal compound of the following general formula (2):

$$CH_2=CHC\equiv CCH=CH(CH_2)_nCHO \qquad (2)$$

wherein n represents an integer of 0 to 11,
the process comprising a step of
hydrolyzing a dialkoxyalkadienyne compound of the following general formula (1):

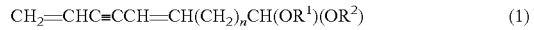

$$CH_2=CHC\equiv CCH=CH(CH_2)_nCH(OR^1)(OR^2) \qquad (1)$$

wherein $R^1$ and $R^2$ represent independently of each other, a monovalent hydrocarbon group having 1 to 15 carbon atoms, preferably 1 to 8, mere preferably 1 to 4, or $R^1$ and $R^2$ may be bonded to each other to form a divalent hydrocarbon group, $R^1$-$R^2$, having from 2 to 10 carbon atoms, and n represents an integer of 0 to 11,
to obtain the dienynal compound (2).

According to another aspect of the present invention, there is provided a process for preparing a dialkoxyalkadienyne compound of the following general formula (1):

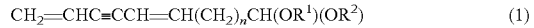

$$CH_2=CHC\equiv CCH=CH(CH_2)_nCH(OR^1)(OR^2) \qquad (1)$$

wherein $R^1$ and $R^2$ represent, independently of each other, a monovalent hydrocarbon group having 1 to 15 carbon atoms, preferably 1 to 8, more preferably 1 to 4, or $R^1$ and $R^2$ may be bonded to each other to form a divalent hydrocarbon group, $R^*$—$R^2$, having from 2 to 10 carbon atoms, and n represents an integer of 0 to 11,
the process comprising a step of
subjecting 4-penten-2-ynal of the following formula (3):

$$CH_2=CHC\equiv CCHO \qquad (3)$$

to a Wittig reaction with a triarylphosphonium dialkoxyalkylide compound of the following general formula (4):

$Ar_3P^+C^-H(CH_2)_nCH(OR^1)(OR^2)$ (4)

wherein Ar may be same as or different from each other and represents an aryl group, and $R^1$ and $R^2$ are as defined above, and n represents an integer of 0 to 11,
to obtain the dialkoxyalkadienyne compound (1).

According to another aspect of the present invention, there is provided a dialkoxyalkadienyne compound of the following general formula (1)

$CH_2$=$CHC$≡$CCH$=$CH(CH_2)_nCH(OR^1)(OR^2)$ (1)

wherein $R^1$ and $R^2$ represent independently of each other, a monovalent hydrocarbon group having 1 to 15 carbon atoms, preferably 1 to 8, more preferably 1 to 4, or $R^1$ and $R^2$ may be bonded to each other to form a divalent hydrocarbon group, $R^1$-$R^2$, having from 2 to 10 carbon atoms, and n represents an integer of 0 to 11.

The dialkoxyalkadienyne compound according to the present invention is useful in the preparation of a dienynal compound.

Further, the dienynal compound is prepared by tire method according to the present invention in a short process and in a high yield, without an oxidation reaction.

DETAILED DESCRIPTION OF THE INVENTION

Dialkoxyalkadienyne Compound (1)

First, the dialkoxyalkadienyne compound of the following general formula (1) will be explained.

$CH_2$=$CHC$≡$CCH$=$CH(CH_2)_nCH(OR^1)(OR^2)$ (1)

wherein, $R^1$ and $R^2$ in the dialkoxyalkadienyne compound (1) represent, independently of each other, a monovalent hydrocarbon group having 1 to 15 carbon atoms, preferably 1 to 8, more preferably 1 to 4, or $R^1$ and $R^2$ may be bonded to each other to form a divalent hydrocarbon group, $R^1$-$R^2$, having from 2 to 10 carbon atoms.

Examples of a monovalent hydrocarbon group include linear saturated hydrocarbon groups such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, and an n-dodecyl group; branched saturated hydrocarbon groups such as an isopropyl group, a 2-methylpropyl group, and 2-methybutyl group; linear unsaturated hydrocarbon groups such as a 2-propenyl group; branched unsaturated hydrocarbon groups such as a 2-methyl-2-propenyl group; cyclic saturated hydrocarbon groups such as a cyclopropyl group; and their isomers. A part of the hydrogen atoms in these hydrocarbon groups may be substituted with a methyl group or an ethyl group.

A methyl group, an ethyl group, an n-propyl group, and an n-butyl group are preferred in view of handling.

Examples of the divalent hydrocarbon group include linear saturated hydrocarbon groups such as an ethylene group, a 1,3-propylene group, and a 1,4-butylene group; branched saturated hydrocarbon groups such as a 1,2-propylene group, a 2,2-dimethyl-1,3-propylene group, a 1,2-butylene group, a 1,3-butylene group, a 2,3-butylene group, and a 2,3-dimethyl-2,3-butylene group; linear unsaturated hydrocarbon groups such as a 1-vinylethylene group; branched unsaturated hydrocarbon groups such as a 2-methyl-1,3-propylene group; cyclic unsaturated hydrocarbon groups such as a 1,2-cyclopropylene group and a 1,2-cyclobutylene group; and their isomers. A part of the hydrogen atoms in these hydrocarbon groups may be substituted with a methyl group or an ethyl group.

In view of the reactivity in elimination of a leaving group, easiness of purification, and availability, the divalent hydrocarbon group is preferably a lower hydrocarbon group, preferably having 2 to 4 carbon atoms. These have high reactivity, and their by-products generated by deprotection are easily removable by water washing or evaporation.

Then, preferred examples of the divalent hydrocarbon group include an ethylene group, a 1,2-propylene group, a 1,3-propylene group, a 1,2-butylene group, a 1,3-butylene group, and a 2,3-dimethyl-2,3-butylene group.

"n" in formula (1) represents an integer of 0 to 11, preferably 2 to 9.

The geometric isomers of the dialkoxyalkadienyne compound (1) are (Z)-dialkoxyalkadienyne compound of the following general formula (1-Z). (E)-dialkoxyalkadienyne compound of the following general formula (1-E), and mixtures thereof.

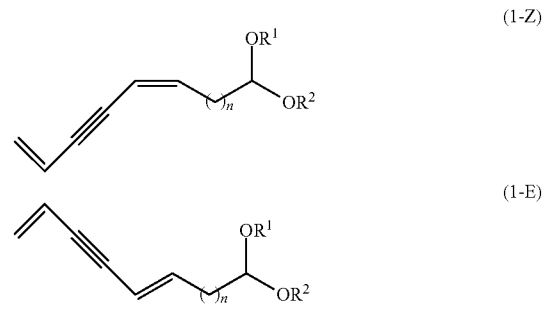

Examples of the dialkoxyalkadienyne compound (1) include a 7,7-dialkoxy-1,5-heptadien-3-yne compound (n=0), an 8,8-dialkoxy-1,5-octadien-3-yne compound (n=1), a 9,9-dialkoxy-1,5-nonadien-3-yne compound (n=2), a 10,10-dialkoxy-1,5-decadien-3-yne compound (n=3), a 11,11-dialkoxy-1,5-undecadien-3-yne compound (n=4), a 12,12-dialkoxy-1,5-dodecadien-3-yne compound (n=5), a 13,13-dialkoxy-1,5-tridecadien-3-yne compound (n=6), a 14,14-dialkoxy-1,5-tetradecadien-3-yne compound (n=7), a 15,15-dialkoxy-1,5-pentadecadien-3-yne compound (n=8), a 16,16-dialkoxy-1,5-hexadecadien-3-yne compound (n=9), a 17,17-dialkoxy-1,5-heptadecadien-3-yne compound (n=10) and an 18,18-dialkoxy-1,5-octadecadien-3-yne compound (n=1).

Specific examples of the 7,7-dialkoxy-1,5-heptadien-3-yne compound (n=0) include a 7,7-dialkoxy-(5Z)-1,5-heptadien-3-yne compound such as 7,7-diethoxy-(5Z)-1,5-heptadien-3-yne; and a 7,7-dialkoxy-(5E)-1,5-heptadien-3-yne compound such as 7,7-diethoxy-(5E)-1,5-heptadien-3-yne.

Specific examples of the 8,8-dialkoxy-1,5-octadien-3-yne compound (n=1) include an 8,8-dialkoxy-(5Z)-1,5-octadien-3-yne compound such as 8,8-diethoxy-(5Z)-1,5-octadien-3-yne; and an 8,8-dialkoxy-(5E)-1,5-octadien-3-yne compound such as 8,8-diethoxy-(5E)-1,5-octadien-3-yne.

Specific examples of the 9,9-dialkoxy-1,5-nonadien-3-yne compound (n=2) include a 9,9-dialkoxy-(5Z)-1,5-nonadien-3-yne compound such as 9,9-dimethoxy-(5Z)-1,5-nonadien-3-yne, 9,9-diethoxy-(5Z)-1,5-nonadien-3-yne, 9,9-dipropoxy-(5Z)-1,5-nonadien-3-yne, 9,9-dibutoxy-(5Z)-1,5-nonadien-3-yne, 9,9-dipentoxy-(5Z)-1,5-nonadien-3-yne, 9,9-dihexoxy-(5Z)-1,5-nonadien-3-yne, 9,9-diheptoxy-(5Z)-1,5-nonadien-3-yne, and 9,9-dioctoxy-(5Z)-1,5-nonadien-3-yne; and a 9,9-dialkoxy-(5E)-1,5-nonadien-3-yne compound such as 9,9-dimethoxy-(5E)-1,5-nonadien-3-yne, 9,9-diethoxy-(5E)-1,5-nonadien-3-yne, 9,9-dipropoxy-(5E)-1,5-nonadien-3-yne, 9,9-dibutoxy-(5E)-1,5-nonadien-3-yne, 9,9-dipentoxy-(5E)-1,5-nonadien-3-yne, 9,9-dihexoxy-(5E)-1,5-nonadien-3-yne, 9,9-diheptoxy-(5E)-1,5-nonadien-3-yne, and 9,9-dioctoxy-(5E)-1,5-nonadien-3-yne.

Specific examples of the 10,10-dialkoxy-1,5-decadien-3-yne compound (n=3) include a 10,10-dialkoxy-(5Z)-1,5-decadien-3-yne compound such as 10,10-diethoxy-(5Z)-1,5-decadien-3-yne; and a 10,10-dialkoxy-(5E)-1,5-decadien-3-yne compound such as 10,10-diethoxy-(5E)-1,5-decadien-3-yne.

Specific examples of the 11,11-dialkoxy-1,5-undecadien-3-yne compound (n=M) include a 11,11-dialkoxy-(5Z)-1,5-undecadien-3-yne compound such as 11,11-dimethoxy-(5Z)-1,5-undecadien-3-yne, 11,11-diethoxy-(5Z)-1,5-undecadien-3-yne, 11,11-dipropoxy-(5Z)-1,5-undecadien-3-yne, 11,11-dibutoxy-(5Z)-1,5-undecadien-3-yne, 11,11-dipentoxy-(5Z)-1,5-undecadien-3-yne, 11,11-dihexoxy-(5Z)-1,5-undecadien-3-yne, 11,11-diheptoxy-(5Z)-1,5-undecadien-3-yne and 11,11-dioctoxy-(5Z)-1,5-undecadien-3-yne; and a 11,11-dialkoxy-(5E)-1,5-undecadien-3-yne compound such as 11,11-dimethoxy-(5E)-1,5-undecadien-3-yne, 11,11-diethoxy-(5E)-1,5-undecadien-3-yne, 11,11-dipropoxy-(5E)-1,5-undecadien-3-yne, 11,11-dibutoxy-(5E)-1,5-undecadien-3-yne, 11,11-diheptoxy-(5E)-1,5-undecadien-3-yne, 11,11-dihexoxy-(5E)-1,5-undecadien-3-yne, 11,11-diheptoxy-(5E)-1,5-undecadien-3-yne and 11,11-dioctoxy-(5E)-1,5-undecadien-3-yne.

Specific examples of the 12,12-dialkoxy-1,5-dodecadien-3-yne compound (n=5) include a 12,12-dialkoxy-(5Z)-1,5-dodecadien-3-yne compound such as 12,12-diethoxy-(5Z)-1,5-dodecadien-3-yne; and a 12,12-dialkoxy-(5E)-1,5-dodecadien-3-yne compound such as 12,12-diethoxy-(5E)-1,5-dodecadien-3-yne.

Specific examples of the 13,13-dialkoxy-1,5-tridecadien-3-yne compound (n=6) include a 13,13-dialkoxy-(5Z)-1,5-tridecadien-3-yne compound such as 13,13-diethoxy-(5Z)-1,5-tridecadien-3-yne, and a 13,13-dialkoxy-(5E)-1,5-tridecadien-3-yne compound such as 13,13-diethoxy-(5E)-1,5-tridecaene-3-yne.

Specific examples of the 14,14-dialkoxy-1,5-tetradecadien-3-yne compound (n=7) include a 14,14-dialkoxy-(5Z)-1,5-tetradecadien-3-yne compound such as 14,14-dimethoxy-(5Z)-1,5-tetradecadien-3-yne, 14,14-diethoxy-(5Z)-1,5-tetradecadien-3-yne, 14,14-dipropoxy-(5Z)-1,5-tetradecadien-3-yne, 14,14-dibutoxy-(5Z)-1,5-tetradecadien-3-yne, 14,14-dipentoxy-(5Z)-1,5-tetradecadien-3-yne, 14,14-dihexoxy-(5Z)-1,5-tetradecadien-3-yne, 14,14-diheptoxy-(5Z)-1,5-tetradecadien-3-yne, and 14,14-dioctoxy-(5Z)-1,5-tetradecadien-3-yne; and a 14,14-dialkoxy-(5E)-1,5-tetradecadien-3-yne compound such as 14,14-dimethoxy-(5E)-1,5-tetradecadien-3-yne, 14,14-diethoxy-(5E)-1,5-tetradecadien-3-yne, 14,14-dipropoxy-(5E)-1,5-tetradecadien-3-yne, 14,14-dibutoxy-(5E)-1,5-tetradecadien-3-yne, 14,14-dipentoxy-(5E)-1,5-tetradecadien-3-yne, 14,14-dihexoxy-(5E)-1,5-tetradecadien-3-yne, 14,14-diheptoxy-(5E)-1,5-tetradecadien-3-yne, and 14,14-dioctoxy-(5E)-1,5-tetradecadien-3-yne.

Specific examples of the 15,15-dialkoxy-1,5-pentadecadien-3-yne compound (n=8) include a 15,15-dialkoxy-(5Z)-1,5-pentadecadien-3-yne compound such as 15,15-diethoxy-(5Z)-1,5-pentadecadien-3-yne; and a 15,15-dialkoxy-(5E)-1,5-pentadecadien-3-yne compound such as 15,15-diethoxy-(5E)-1,5-pentadecadien-3-yne.

Specific examples of the 16,16-dialkoxy-1,5-hexadecadien-3-yne compound (n=9) include a 16,16-dialkoxy-(5Z)-1,5-hexadecadien-3-yne compound such as 16,16-diethoxy-(5Z)-1,5-hexadecadien-3-yne; and a 16,16-dialkoxy-(5E)-1,5-hexadecadien-3-yne compound such as 16,16-diethoxy-(5E)-1,5-hexadecadien-3-yne.

Specific examples of the 17,17-dialkoxy-1,5-heptadecadien-3-yne compound (n=10) include a 17,17-dialkoxy-(5Z)-1,5-heptadecadien-3-yne compound such as 17,17-diethoxy-(5Z)-1,5-heptadecadien-3-yne; and a 7,17-dialkoxy-(5E)-1,5-heptadecadien-3-yne compound such as 17,17-diethoxy-(5E)-1,5-heptadecadien-3-yne.

Specific examples of the 18,18-dialkoxy-1,5-octadecadien-3-yne compound (n=11) include an 18,18-dialkoxy-(5Z)-1,5-octadecadien-3-yne compound such as 18,18-diethoxy-(5Z)-1,5-octadecadien-3-yne; and an 18,18-dialkoxy-(5E)-1,5-octadecadien-3-yne compound such as 18,18-diethoxy-(5E)-1,5-octadecadien-3-yne.

Preparation of the Dialkoxyalkadienyne Compound (1) by a Wittig Reaction

The dialkoxyalkadienyne compound (1) may be prepared by a Wittig reaction of 4-penten-2-ynal of the blowing formula (3) with a triarylphosphonium dialkoxyalkylide of the following general formula (4), to obtain the dialkoxyalkadienyne compound (1), as shown in the following chemical reaction formula.

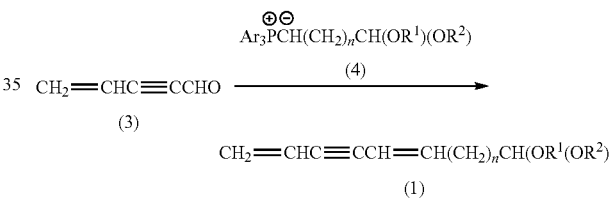

4-Penten-2-ynal (3)

4-Penten-2-ynal (3) may be prepared, for example, by hydrolyzing a 5,5-dialkoxy-1-penten-3-yne compound of the following general formula (5), as shown in the following chemical reaction formula.

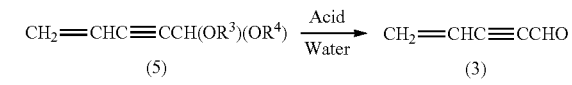

$R^3$ and $R^4$ represent, independent of each other, a monovalent hydrocarbon group having 1 to 15 carbon atoms, preferably 1 to 8, mere preferably 1 to 4, or $R^3$ and $R^4$ may be bonded to each other to form a divalent hydrocarbon group, $R^3$-$R^4$, having from 2 to 10 carbon atoms.

Examples of $R^3$ and $R^4$ are same as the examples of $R^1$ and $R^2$ in the dialkoxyalkadienyne compound (1).

Examples of the 5,5-dialkoxy-1-penten-3-yne compound (5) include 5,5-dimethoxy-1-penten-3-yne, 5,5-diethoxy-1-penten-3-yne, 5,5-dipropoxy-1-penten-3-yne, 5,5-dibutoxy-1-penten-3-yne, 5,5-ethoxymethoxy-1-penten-3-yne, 1-penten-3-yne-1,3-dioxolane, and 1-pentene-3-yne-1,3-dioxane. 5,5-Dimethoxy-1-penten-3-yne, 5,5-diethoxy-1-penten-3-yne, 5,5-dipropoxy-1-penten-3-yne, and 5,5-dibutoxy-1-penten-3-yne are preferred in view of versatility.

The 5,5-dialkoxy-1-penten-3-yne compound (5) may be synthesized, for example, by eliminating a leaving group Z at position 5 of a 2-ynal acetal compound of the following general formula (6) in the presence of a base, as shown in the following chemical reaction formula.

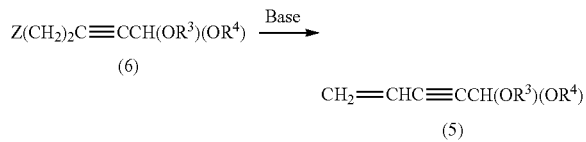

$Z(CH_2)_2C\equiv CCH(OR^3)(OR^4) \xrightarrow{\text{Base}}$ (6)

$CH_2=CHC\equiv CCH(OR^3)(OR^4)$ (5)

$R^3$ and $R^4$ in the 2-ynal acetal compound (6) represent, independently of each other, a monovalent hydrocarbon group having 1 to 15 carbon atoms, preferably 1 to 8, more preferably 1 to 4, or $R^3$ and $R^4$ may be bonded to each other to form a divalent hydrocarbon group, $R^3$-$R^4$, having from 2 to 10 carbon atoms.

Where $R^3$ and $R^4$ in the 2-ynal acetal compound (6) are a monovalent hydrocarbon group or a divalent hydrocarbon group, $R^3$ and $R^4$ may be selected from the options for $R^1$ and $R^2$ in the dialkoxyalkadienyne compound (1).

Z in the 2-ynal acetal compound (6) represents a leaving group and is an alkoxy group having 1 to 12 carbon atoms, an acyloxy group having 1 to 10 carbon atoms, a silyloxy group having 3 to 20 carbon atoms, an alkanesulfonyloxy group having 1 to 10 carbon atoms, an arenesulfonyloxy group having 6 to 20 carbon atoms, or a halogen atom.

The number of the carbon atoms of the alkoxy group is 1 to 12, preferably 1 to 9.

Examples of the alkoxy group include linear saturated alkoxy groups such as a methoxy group, an ethoxy group, an n-propoxy group, an n-butoxy group, and an n-pentyloxy group; branched saturated alkoxy groups such as ail isopropoxy group and a t-butoxy group; linear unsaturated alkoxy groups such as a 2-propenyloxy group and a 2-propynyloxy group; branched unsaturated alkoxy groups such as a 2-methyl-2-propenyloxy group; cyclic alkoxy groups such as a cyclopropyloxy group, a 2-methylcyclopropoxy group, a cyclobutyloxy group, and a cyclopentyloxy group; alkoxy groups comprising an aromatic ring such as a benzyloxy group and a p-methoxybenzyloxy group; alkoxyalkoxy groups such as a methoxymethoxy group, a methoxyethoxy group; a 2-methoxyethoxymethoxy group, a benzyloxymethoxy group, a p-methoxybenzoyloxymethoxy group, a 1-ethoxyethoxy group, and a tetrahydropyran-2-yloxy group; and halogenated alkoxy groups such as a 2,2,2-trichloroethoxy group and a pentafluoroethoxy group; and their isomers. A part of the hydrogen atoms in these alkoxy groups may be substituted with a methyl group or an ethyl group.

Particularly preferable examples of the alkoxy group include a methoxy group, an ethoxy group, a 2-propenyloxy group, a methoxymethoxy group, a methoxyethoxy group, and a 1-ethoxyethoxy group because of their availability, and because byproducts formed in the deprotection are easily removed by water washing or evaporation.

The number of the carbon atoms of the acyloxy group is 1 to 10, preferably 1 to 7.

Examples of the acyloxy group include linear aliphatic acyloxy groups such as a formyloxy group, an acetoxy group, a propanoyloxy group, a butanoyloxy group, and a crotonyloxy group; branched aliphatic acyloxy groups such as a 2-methylpropionyloxy group and a pivaloyloxy group; halogenated acyloxy groups such as a trichloroacetoxy group and a trifluoroacetoxy group; and aromatic acyloxy groups such as a benzoyloxy group; and their isomers. A part of the hydrogen atoms in these acyloxy groups may be substituted with a methyl group or an ethyl group.

Particularly preferable examples of the acyloxy group include an acetoxy group, a propanoyloxy group, a pivaloyloxy group; and a benzoyloxy group in view of the availability.

The number of the carbon atoms of the silyloxy group is 3 to 20, preferably 3 to 16, more preferably 3 to 10.

Examples of the silyloxy group include trialkylsilyloxy groups such as a trimethylsilyloxy group, a triethylsilyloxy group, a triisopropylsilyloxy group, and a t-butyldimethylsilyloxy group; and monoalkyldiarylsilyloxy groups such as a t-butyldiphenylsilyloxy group; and their isomers. A part of the hydrogen atoms in these silyloxy groups may be substituted with a methyl group or an ethyl group.

Particularly preferable examples of the silyloxy group include a trimethylsilyloxy group, a triethylsilyloxy group in view of the availability, and in view of the feet that byproducts generated by deprotection can be easily removed by washing or concentration.

The number of the carbon atoms of the alkanesulfonyloxy group is 1 to 10, preferably 1 to 7.

Examples of the alkanesulfonyloxy group include a methanesulfonyloxy group, an ethanesulfonyloxy group, a 1-butanesulfonyloxy group, a 1-octanesulfonyloxy group, an allylsulfonyloxy group, a 10-camphorsulfonyloxy group, a trifluoromethanesulfonyloxy group, and a benzylsulfonyloxy group; and their isomers. A part of the hydrogen atoms in these alkanesulfonyloxy groups may be substituted with a methyl group or an ethyl group.

Particularly preferable examples of the alkanesulfonyloxy group include a methanesulfonyloxy group and an ethanesulfonyloxy group in view of the availability.

The number of the carbon atoms of the arenesulfonyloxy group is 6 to 20, preferably 6 to 15, more preferably 6 to 7.

Examples of the arenesulfonyloxy group include a benzenesulfonyloxy group, a 4-chlorobenzenesulfonyloxy group, a 4-methoxybenzenesulfonyloxy group, a 2-nitrobenzenesulfonyloxy group, a 2,4,6-trimethylbenzenesulfonyloxy group, a p-toluenesulfonyloxy group, a 1-naphthalenesulfonyloxy group, and a 2-naphthalenesulfonyloxy group; and their isomers. A part of the hydrogen atoms in these arenesulfonyloxy groups may be substituted with a methyl group or an ethyl group.

Particularly preferred examples of the arenesulfonyloxy group include a benzenesulfonyloxy group and a p-toluenesulfonyloxy group in view of the availability.

Examples of the halogen atoms include a fluorine atom, a chlorine atom, a bromine atom and an iodine atom.

Particularly preferred examples of the halogen atoms are a chlorine atom and a bromine atom in view of the availability.

Specific examples of the 2-ynal acetal compound (6) with Z being an alkoxy group having 1 to 12 carbon atoms include a 1,1-dialkoxy-5-(methoxymethoxy)-2-pentyne compound such as 1,1-dimethoxy-5-(methoxymethoxy)-2-pentyne and 1,1-diethoxy-5-(methoxymethoxy)-2-pentyne; a 1,1-dialkoxy-5-(methoxyethoxy)-2-pentyne compound such as 1,1-dimethoxy-5-(methoxyethoxy)-2-pentyne, 1,1-diethoxy-5-(methoxyethoxy)-2-pentyne; a 1,1-dialkoxy-5-methoxy-2-pentyne confound such as 1,1-dimethoxy-5-methoxy-2-pentyne and 1,1-diethoxy-5-methoxy-2-pentyne; and a 1,1-dialkoxy-5-ethoxy-2-pentyne compound such as 1,1-dimethoxy-5-ethoxy-2-pentyne and 1,1-diethoxy-5-ethoxy-2-pentyne.

Specific examples of the 2-ynal acetal compound (6) with Z being ail acyloxy group having 1 to 10 carbon atoms include a 1,1-dialkoxy-5-acetyloxy-2-pentyne compound such as 1,1-dimethoxy-5-acetyloxy-2-pentyne and 1,1-diethoxy-5-acetyloxy-2-pentyne.

Specific examples of the 2-ynal acetal compound (6) with Z being a silyloxy group having 3 to 20 carbon atoms include a 1,1-dialkoxy-5-trimethylsilyloxy-2-pentyne compound such as 1,1-dimethoxy-5-trimethylsilyloxy-2-pentyne and 1,1-diethoxy-5-trimethylsilyloxy-2-pentyne; a 1,1-dialkoxy-5-triethylsilyloxy-2-pentyne compound such as 1,1-dimethoxy-5-triethylsilyloxy-2-pentyne and 1,1-diethoxy-5-triethylsilyloxy-2-pentyne.

Specific examples of the 2-ynal acetal compound (6) with Z being an alkanesulfonyloxy group having 1 to 10 carbon atoms include a 1,1-dialkoxy-5-methanesulfonyloxy-2-pentyne compound such as 1,1-dimethoxy-5-methanesulfonyloxy-2-pentyne, and 1,1-diethoxy-5-methanesulfonyloxy-2-pentyne.

Specific examples of the 2-ynal acetal compound (6) with Z being an arenesulfonyloxy group having 6 to 20 carbon atoms include a 1,1-dialkoxy-5-(p-toluenesulfonyloxy)-2-pentyne compound such as 1,1-dimethoxy-5-(p-toluenesulfonyloxy)-2-pentyne and 1,1-diethoxy-5-(p-toluenesulfonyloxy)-2-pentyne.

Specific examples of the 2-ynal acetal compound (6) with Z being a halogen atom include a 1,1-dialkoxy-5-chloro-2-pentyne compound such as 1,1-dimethoxy-5-chloro-2-pentyne and 1,1-diethoxy-5-chloro-2-pentyne; and a 1,1-dialkoxy-5-bromo-2-pentyne compound such as 1,1-dimethoxy-5-bromo-2-pentyne and, 1,1-diethoxy-5-bromo-2-pentyne.

An acidity at position 4 in the 2-ynal acetal compound (6) is highly increased by the electronic effects of the acetal group and the triple bond, so that an elimination reaction of the leaving group Z may take place, even when the leaving group Z is an alkoxy, acyloxy or silyloxy group which has a low leaving ability, without need to convert the leaving group into another leaving group having a high leaving ability and, as a matter of course, also when the leaving group Z is an alkanesulfonyloxy group, an arenesulfonyloxy group or a halogen atom which all have a high leaving ability.

In a case where the leaving Z is an alkoxy group, acyloxy group, or silyloxy group which have a low leaving ability, the advantage of the 2-ynal-acetal compound (6) has a high thermal stability, compared with an alkanesulfonyloxy group, an arenesulfonyloxy group and a halogen atom, and, therefore, industrially advantageous purification by distillation is easy.

Meanwhile, in the compound having a hydrocarbon group instead of au acetal group, the acidity at the 4-position does not increase, so that an damnation reaction does not proceed particularly efficiently with an alkoxy group, an acyloxy group or a silyloxy group winch have a low elimination ability.

Examples of the base to be used in the elimination reaction of the leaving group Z include hydroxides such as sodium hydroxide, potassium hydroxide, calcium hydroxide and magnesium hydroxide; metal alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic reagents such as methyllithium, ethyllithium, n-butyllithium, methylmagnesium chloride, sodium dimsyl sodium, sodium acetylide, and potassium acetylide; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydrides such as sodium hydride; potassium hydride, and calcium hydride; and amines such as triethylamine, piperidine, pyrrolidine, pyridine, 4-dimethylaminopyridine, and 1,8-diazabicyclo[5.4.0]-7-undecene (DBU).

Preferable examples of the base include metal alkoxides such as sodium methoxide, sodium ethoxide, and potassium t-butoxide in view of suppressing the formation of allene compounds and impurities so as to obtain the 4-penten-2-ynal (3) in a high yield.

The base may be used either alone or in combination thereof. The base may be commercially available one.

An amount of the base is preferably from 0.6 to 3.0 mol, more preferably from 0.7 to 2.0 mol, and even more preferably from 0.8 to 1.5 mol, per mol of the 2-ynal acetal compound (6).

A solvent may be used in the elimination reaction, if necessary.

Examples of the solvent include ethers such as diethyl ether, dibutyl ether, tetrahydrofuran (THF), 4-methyltetrahydropyran, cyclopentyl methyl ether, and 1,4-dioxane; hydrocarbons such as hexane, heptane, benzene, toluene, xylene, and cumene; chloride solvents such as methylene chloride, chloroform, and trichloroethylene aprotic polar solvents such as N,N-dimethylformamide (DMF), N,N-dimethylacetamide, N-methylpyrrolidone, dimethyl sulfoxide γ-butyrolactone, 1,3-dimethyl-2-imidazolidinone, and hexamethylphosphoric triamide; nitriles such as acetonitrile and propionitrile; esters such as ethyl acetate and n-butyl acetate; and alcohols such as methanol, ethanol, and t-butyl alcohol The solvent may be used either alone or in combination thereof. The solvent may be commercially available one.

An amount of the solvent is preferably from 0 to 10,000 g, more preferably from 0 to 5,000 g, per mol of the 2-ynal acetal compound (6).

When the base is a metal alkoxide, organometallic reagent metal amide, or metal hydride, a temperature of the elimination reaction is preferably from −78 to 70° C., more preferably from −50 to 40° C., and even more preferably −30 to 30° C., in view of the yield.

When the base is an amine, the temperature of the elimination reaction is preferably from 0 to 180° C., more preferably from 10 to 150° C., even more preferably from 20 to 130° C., in view of the yield.

A reaction time of the elimination may vary, depending on a solvent or a production scale, and is preferably from 0.5 to 55 hours in view of the reactivity.

The hydrolysis reaction of the 5,5-dialkoxy-1-penten-3-yne compound (5) may be carried out using, for example, an acid or water.

Examples of the acid include inorganic acids such as hydrochloric acid and hydrobromic acid; and organic acids such as p-toluenesulfonic acid (p-TsOH), benzenesulfonic acid, trifluoroacetic acid, acetic acid, formic acid and oxalic acid; and iodotrimethylsilane and titanium tetrachloride with p-toluenesulfonic acid and oxalic acid being preferred in view of the reactivity.

The acid may be used either alone or in combination thereof. The acids may be commercially available one.

An amount of the acid is preferably 0.001 to 10.0 mol per mol of the 5,5-dialkoxy-1-penten-3-yne compound (5), in view of the completion of the reaction.

An amount of water is preferably from 18 to 3.000 g per mol of the 5,5-dialkoxy-1-penten-3-yne compound (5), in view of the completion of the reaction.

A solvent may be used in the hydrolysis, if necessary, together with the aforesaid acid or water.

Examples of the solvent include hydrocarbon solvents such as toluene, xylene, hexane, heptane, benzene, and cumene; ether solvents such as tetrahydrofuran, diethyl ether, dibutyl ether, 4-methyltetrahydropyran, cycloheptylmethyl ether, and 1,4-dioxane; polar solvents such as N,N-dimethylfomamide, N,N-dimethylacetamide, N-methylpyrolidone, dimethyl sulfoxide, acetonitrile, acetone, γ-butyrolactone, dichloromethane and chloroform; and alcohols such as methanol and ethanol.

The solvent may be used either alone or in combination thereof. The solvent may be commercially available one.

An optimum solvent varies, depending on an acid used. For instance, when p-toluenesulfonic acid is used as the acid, the solvent is preferably tetrahydrofuran in view of the reactivity.

An amount of the solvent is preferably from 0 to 3,000 g per mol of the 5,5-dialkoxy-1-penten-3-yne compound (5) in view of the reactivity.

An antioxidant may be used in the hydrolysis, if necessary, together with the aforesaid acid or water.

Examples of the antioxidant include dibutylhydroxytoluene (BHT), vitamin A, vitamin C, vitamin E, uric acid, glutathione, and meladonin.

An amount of the antioxidant is preferably from 0.001 to 1,000 g per mol of the 5,5-dialkoxy-1-penten-3-yne compound (5) in view of the yield.

The antioxidant may be used either alone or in combination thereof. The antioxidant may be commercially available one.

A reaction temperature in the hydrolysis reaction varies, depending on the acid or solvent used, and is preferably 5 to 180° C. in view of the reactivity.

A reaction time in the hydrolysis reaction varies, depending on the solvent used or the production scale, and is preferably 0.5 to 55 hours in view of the reactivity.

Triarylphosphonium Dialkoxyalkylide Compound (4)

The triarylphosphonium dialkoxyalkylide compound is represented by the following general formula (4).

$$Ar_3P^+C^-H(CH_2)_nCH(OR^1)(OR^2) \quad (4)$$

$R^1$ and $R^2$ in the triarylphosphonium dialkoxyalkylide compound (4) represent, independently of each other, a monovalent hydrocarbon group having 1 to 15 carbon atoms, preferably 1 to 8, more preferably 1 to 4, or $R^1$ and $R^2$ may be bonded to each other to form a divalent hydrocarbon group, $R^1$-$R^2$ having from 2 to 10 carbon atoms.

Examples of $R^1$ and $R^2$ are same as the examples of $R^1$ and $R^2$ in the dialkoxyalkadienyne compound (1).

"n" in formula (4) represents an integer of 0 to 11, preferably 2 to 9.

Ar in the triarylphosphonium dialkoxyalkylide compound (4) represents an aryl group which may be the same as or different from each other. The number of the carbon atoms of the aryl group is preferably 6 to 24, more preferably 6 to 12, and even more preferably 6 or 7.

Examples of the aryl group include a phenyl group (Ph group), a tolyl group, a naphtyl group and an anthracenyl group, with a phenyl group being preferred in view of easiness of the synthesis. It is preferred that all of the three aryl groups are a phenyl group in view of easiness of the synthesis.

Examples of the triarylphosphonium dialkoxyalkylide compound (4) include a triarylphosphonium 2,2-dialkoxyethylide compound (n=0), a triarylphosphonium 3,3-dialkoxypropylide compound (n=1), a triaryl phosphonium 4,4-dialkoxybutylide compound (n=2), a triarylphosphonium 5,5-dialkoxypentylide compound (n=3), a triarylphosphonium 6,6-dialkoxyhexylide compound (n=4), a triarylphosphonium 7,7-dialkoxyheptylide compound (n=5), a triarylphosphonium 8,8-dialkoxyoctylide compound (n=6), a triarylphosphonium 9,9-dialkoxynonylide compound (n=7), a triarylphosphonium 10,10-dialkoxydecylide compound (n=8), a triarylphosphonium 11,11-dialkoxyundecylide compound (n=9), a triarylphosphonium 12,12-dialkoxydodecylide compound (n=10), and a triarylphosphonium 13,13-dialkoxytridecylide compound (n=11).

Specific examples of the triarylphosphonium 22-dialkoxyethylide compound (n=0) include triphenylphosphonium 2,2-dimethoxyethylidene and triphenylphosphonium 22-diethoxyethylene.

Specific examples of the triarylphosphonium 3,3-dialkoxypropylide compound (n=1) include triphenylphosphonium 3,3-dimethoxypropylide and 3,3-triphenylphosphonium diethoxypropylide.

Specific examples of the triarylphosphonium dialkoxybutylide compound (n=2) include a triphenylphosphonium 4,4-dialkoxybutylide compound such as triphenylphosphonium 4,4-dimethoxybutylide, triphenylphosphonium 4,4-diethoxybutylide, triphenylphosphonium 4,4-dipropoxybutylide, and triphenylphosphonium 4,4-dibutoxybutylide; and a tritolylphosphonium 4,4-dialkoxybutylide compound such as tritolylphosphonium 4,4-dimethoxybutylide, tritolylphosphonium 4,4-diethoxybutylide, tritolylphosphonium 4,4-dipropoxybutylide, and tritolylphosphonium 4,4-dibutoxybutylide.

Specific examples of the triarylphosphonium 5,5-dialkoxypentylide compound (n=3) include triphenylphosphonium 5,5-dimethoxypentylide and triphenylphosphonium 5,5-diethoxypentylide.

Specific examples of the triarylphosphonium 6,6-dialkoxyhexylide compound (n=4) include a triphenylphosphonium 6,6-dialkoxyhexylide compound such as triphenylphosphonium 6,6-dimethoxyhexylide, triphenylphosphonium 6,6-diethoxyhexylide, triphenylphosphonium 6,6-dipropoxyhexylide, and triphenylphosphonium 6,6-dibutoxyhexylide; and a tritolylphosphonium 6,6-dialkoxyhexylide compound such as tritolylphosphonium 6,6-dimethoxyhexylide, tritolylphosphonium 6,6-diethoxyhexylide, tritolylphosphonium dipropoxyhexylide, and tritolylphosphonium 6,6-dibutoxyhexylide.

Specific examples of the triarylphosphonium 7,7-dialkoxyheptylide compound (n=5) include triphenylphosphonium 7,7-dimethoxyheptylide and triphenylphosphonium 7,7-diethoxyheptylide.

Specific examines of the triarylphosphonium 8,8-dialkoxyoctylide compound (n=6) include triphenylphosphonium 8,8-dimethoxyoctylide and triphenylphosphonium 8,8-diethoxyoctylide.

Specific examples of the triarylphosphonium 9,9-dialkoxynonylide compound (n=7) include a triphenylphosphonium 9,9-dialkoxynonylide compound such as triphenylphosphonium 9,9-dimethoxynonylide, triphenylphosphonium 9,9-diethoxynonylide, triphenylphosphonium 9,9-dipropoxynonylide, and triphenylphosphonium 9,9-dibutoxynonylide; and a tritolylphosphonium 9,9-dialkoxynonylide compound such as tritolylphosphonium 9,9-dimethoxynonylide, tritolylphosphonium 9,9-diethoxynonylide, tritolylphosphonium 9,9-dipropoxynonylide, and tritolylphosphonium 9,9-dibutoxynonylide.

Specific examples of the triarylphosphonium 10,10-dialkoxydecylide compound (n=8) include triphenylphosphonium 10,10-dimethoxydecylide and triphenylphosphonium 10,10-diethoxydecylide.

Specific examples of the triarylphosphonium 11,11-dialkoxyundecylide confound (n=9) include triphenylphosphonium 11,11-dimethoxyundecylide and triphenylphosphonium 11,11-diethoxyundecylide.

Specific examples of the triarylphosphonium 12,12-dialkoxydedecylide compound (n=10) include triphenylphosphonium 12,12-dimethoxydodecylide and triphenylphosphonium 12,12-diethoxydodecylide.

Specific examples of the triarylphosphonium 13,13-dialkoxytridecylide compound (n=11) include triphenylphosphonium 13,13-dimethoxytridecylide and triphenylphosphonium 13,13-diethoxytridecylide.

The triarylphosphonium dialkoxyalkylide compound (4) may be used either alone or in combination thereof. The triarylphosphonium dialkoxyalkylide compound (4) may be commercially available one or may be synthesized in house.

For instance, the triarylphosphonium 9,9-dialkoxynonylide compound (4: n=7) may be produced by reacting a 9-halo-1,1-dialkoxynonane compound of the following general formula (7) with a phosphorus compound of the following general formula (8) to obtain a 9,9-dialkoxynonyltriarylphosphonium halide compound of the following general formula (9); and subjecting the 9,9-dialkoxynonyltriarylphosphonium halide compound (9) thus obtained to deprotonation in the presence of a base to obtain the triarylphosphonium 9,9-dialkoxynonylide compound (4: n=7), as shown in the following chemical reaction formula.

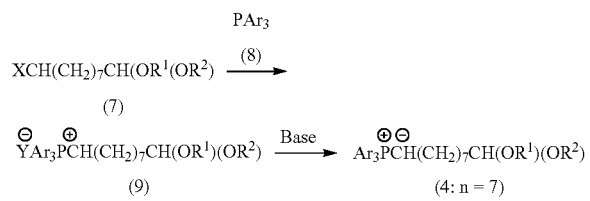

$R^1$ and $R^2$ in the 9-halo-1,1-dialkoxynonane compound (7) represent, independently of each other, a monovalent hydrocarbon group having 1 to 15 carbon atoms, preferably 1 to 8, more preferably 1 to 4, or $R^1$ and $R^2$ may be bonded to each other to form a divalent hydrocarbon group. $R^1$-$R^2$, having from 2 to 10 carbon atoms.

Examples of $R^1$ and $R^2$ are same as the examples of $R^1$ and $R^2$ in the dialkoxyalkadienyne compound (1).

X in the 9-halo-1,1-dialkoxynonane compound (7) represents a halogen atom, such as a chlorine atom, a bromine atom, and an iodine atom, with a chlorine atom and a bromine atom being preferable in view of versatility.

Example of the 9-halo-1,1-dialkoxynonane compound (7) include a 9-chloro-1,1-dialkoxynonane compound such as 9-chloro-1,1-dimethoxynonane, 9-chloro-1,1-diethoxynonane, 9-chloro-1,1-dipropxynonane, 9-chloro-1,1-dibutoxynonane, 9-chloro-1,1-dipentoxynonane, 9-chloro-1,1-dihexoxynonane, 9-chloro-1,1-dipentoxynonane, and 9-chloro-1,1-dioctoxynonane; a 9-bromo-1,1-dialkoxynonane compound such as 9-bromo-1,1-dimethoxynonane, 9-bromo-1,1-diethoxynonane, 9-bromo-1,1-dipropxynonane, 9-bromo-1,1-dibutoxynonane, 9-bromo-1,1-dipentoxynonane, 9-bromo-1,1-dihexoxynonane, 9-bromo-1,1-dipentoxynonane, and 9-bromo-1,1-dioctoxynonane; and a 9-iodo-1,1-dialkoxynonane compound such as 9-iodo-1,1-dimethoxynonane, 9-iodo-1,1-diethoxynonane, 9-iodo-1,1-dipropxynonane, 9-iodo-1,1-dibutoxynonane, 9-iodo-1,1-dipentoxynonane, 9-iodo-1,1-dihexoxynonane, 9-iodo-1,1-dipentoxynonane and 9-iodo-1,1-dioctoxynonane.

$R^1$ and $R^2$ in the a 9-halo-1,1-dialkoxynonane compound (7) represent independently of each other, a monovalent hydrocarbon group having 1 to 15 carbon atoms, preferably 1 to 8, mere preferably 1 to 4, or $R^1$ and $R^2$ may be bonded to each other to form a divalent hydrocarbon group, $R^1$-$R^2$, having from 2 to 10 carbon atoms.

Ar in the phosphorus compound (8) may be same as or different from each other and represent an aryl group. The number of the carbon atoms of the aryl group is preferably 6 to 24, mere preferably 6 to 12, and even more preferably 6 or 7.

Examples of the aryl group include a phenyl group, a tolyl group, a naphtyl group and an anthracenyl group, with a phenyl group being preferable. It is mote preferred that all of the three aryl groups are a phenyl group in view of easiness of the synthesis.

Examples of the phosphorus compound (8) include a triarylphosphine compound such as triphenylphosphine and tritolylphosphine, with triphenylphosphine being preferable in view of the reactivity.

An amount of the phosphorus compound (8) is preferably from 0.8 to 5.0 mol per mol of the 9-halo-1,1-dialkoxynonane compound (7) in view of the reactivity.

A halide may be used, if necessary, in the preparation of the 9,9-dialkoxynonyltriarylphosphonium halide compound (9).

Examples of the halide include sodium iodide, potassium iodide, sodium bromide, and potassium bromide, with iodide such as sodium iodide and potassium iodide being preferable in view of tire reactivity.

The halide may be used either alone or in combination thereof. The halide may be commercially available one.

An amount of the halide to be used is preferably from 0.1 to 5.0 mol per mol of the 9-halo-1,1-dialkoxynonane compound (7) in view of the reactivity.

A base may be added, if necessary, in the preparation of the 9,9-dialkoxynonyltriarylphosphonium halide compound (9).

Examples of the base include alkali metal carbonates such as potassium carbonate and sodium carbonate; alkaline earth metal carbonates such as calcium carbonate and magnesium carbonate; and amines such as triethylamine, tripropylamine, triisopropylamine, tributylamine, N,N-diethylaniline, and pyridine, with alkali metal carbonates being preferable in view of handling.

The base may be used either alone or in combination thereof. The base may be commercially available one.

An amount of the base is preferably from 0.001 to 1.0 mol per mol of the 9-halo-1,1-dialkoxynonane compound (7) in view of the reactivity.

A temperature in the preparation of the 9,9-dialkoxynonyltriarylphosphonium halide compound (9) varies, depending on a solvent used, and is preferably from 60 to 180° C. in view of the reactivity.

A reaction time in the preparation of the 9,9-dialkoxynonyltriarylphosphonium halide compound (9) varies, depending on a solvent used and a production scale, and is preferably from 3 to 55 hours.

R$^1$ and R$^2$ in the 9,9-dialkoxynonyltriarylphosphonium halide compound (9) represent independently of each other, a monovalent hydrocarbon group having 1 to 15 carbon atoms, preferably 1 to 8, mere preferably 1 to 4, or R$^1$ and R$^2$ may be bonded to each other to form a divalent hydrocarbon group, R$^1$-R$^2$, having from 2 to 10 carbon atoms.

Examples of R$^1$ and R$^2$ are same as the examples of R$^1$ and R$^2$ in the dialkoxyalkadienyne compound (1).

Y in the 9,9-dialkoxynonyltriarylphosphonium halide compound (9) represents a halogen atom, and examples thereof include a chlorine atom, a bromine atom, and an iodine atom.

In a case where a halide is not used in the preparation of the 9,9-dialkoxynonyltriarylphosphonium halide compound (9), Y is the halogen atom same as X. In a case where iodide is used as a halide, Y is a halogen atom same as X or an iodine atom.

Ar in the 9,9-dialkoxynonyltriarylphosphonium halide compound (9) represents an aryl group. Ar is as defined for the phosphorus compound (8).

Example of the 9,9-dialkoxynonyltriarylphosphonium halide compound (9) include a 9,9-dialkoxynonyltriphenylphosphonium chloride compound such as 9,9-dimethoxynonyltriphenylphosphonium chloride, 9,9-diethoxynonyltriphenylphosphonium chloride, 9,9-dipropoxynonyltriphenylphosphonium chloride, and 9,9-dibutoxynonyltriphenylphosphonium chloride; a 9,9-dialkoxynonyltriphenylphosphonium bromide compound such as 9,9-dimethoxynonyltriphenylphosphonium bromide, 9,9-diethoxynonyltriphenylphosphonium bromide, 9,9-dipropoxynonyltriphenlphosphonium bromide, and 9,9-dibutoxynonyltriphenylphosphonium bromide; a 9,9-dialkoxynonyltriphenylphosphonium iodide compound such as 9,9-dimethoxynonyltriphenylphosphonium iodide, 9,9-diethoxynonyltriphenylphosphonium iodide, 9,9-dipropoxynonyltriphenylphosphonium iodide, and a 9,9-dibutoxynonyltriphenylphosphonium iodide; a 9,9-dialkoxynonyltritolylphosphonium chloride compound such as 9,9-dimethoxynonytritolylphosphonium dichloride, 9,9-diethoxynonyltritolylphosphonium chloride, 9,9-dipropoxynontritolylphosphonium dichloride, and 9,9-dibutoxynonyltritolylphosphonium chloride; a 9,9-dialkoxynonyltritolylphosphonium bromide compound such as 9,9-dimethoxynonyltritolylphosphonium bromide, 9,9-diethoxynonyltritolylphosphonium bromide, 9,9-dipropoxynonyltritolylphosphonium bromide, and 9,9-dibutoxynonylitritolylphosphonium bromide; and a 9,9-dialkoxynonyltritolylphosphonium iodide compound such as 9,9-dimethoxynonyltritolylphosphonium iodide, 9,9-diethoxynonyltritolylphosphonium iodide, 9,9-dipropoxynonyltritolylphosphonium iodide, and 9,9-dibutoxynonyltritolylphosphonium iodide.

The triarylphosphonium 9,9-dialkoxynonylide compound (4: n=7) is obtained by subjecting the 9,9-dialkoxynonyltriarylphosphonium halide compound (9) thus obtained to deprotonation in the presence of a base.

The triarylphosphonium 9,9-dialkoxynonylide compound (4: n=7) may be prepared by adding a base directly in the reaction system after the preparation of the 9,9-dialkoxynonyltriarylphosphonium halide compound (9). Alternatively the 9,9-dialkoxynonyltriarylphosphonium halide compound (9) is isolated and purified, to which a base is then added to obtain the triarylphosphonium 9,9-dialkoxynonylide compound (4).

Examples of the base to be used in the preparation of the triarylphosphonium 9,9-dialkoxynonylide compound (4: n=7) include alkyllithium such as n-butyllithium and tert-butyllithium; metal alkoxides such as potassium tert-butoxide, sodium tert-butoxide, potassium methoxide, sodium methoxide, potassium ethoxide, sodium ethoxide; and metal amides such as lithium diisopropylamide and sodium bis(trimethylsilyl)amide Metal alkoxides are preferable, particularly potassium tert-butoxide, sodium methoxide, and sodium ethoxide, in view of the reactivity.

An amount of the base is preferably from 0.7 to 5.0 mol per mol of the 9-halo-1,1-dialkoxynonane compound (7) in view of the reactivity.

A temperature in the preparation of the triarylphosphonium 9,9-dialkoxynonylide compound (4: n=7)) varies, depending on the solvent and the base, and is preferably from −78 to 25° C.

A reaction time in the preparation of the triarylphosphonium 9,9-dialkoxynonylide compound (4: n=7) varies, depending on the solvent and the production scale, and is preferably from 0.5 to 50 hours.

A solvent may be used, if necessary, in the preparation of the 9,9-dialkoxynonyltriarylphosphonium halide compound (9) and in the preparation of the triarylphosphonium 9,9-dialkoxynonylide compound (4: n=7).

Examples of the solvent include ether solvents such as tetrahydrofuran, diethyl ether, dibutyl ether, 4-methyltetrahydropyran, cyclopentyl methyl ether, and 1,4-dioxane; hydrocarbon solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform, with the ether solvents such as tetrahydrofuran and the polar solvents such as acetonitrile and N,N-dimethylacetamide being preferable in view of the reactivity.

The solvent may be used either alone or in combination thereof. The solvent may be commercially available one.

An amount of the solvent is preferably from 50 to 5,000 g per mol of the 9-halo-1,1-dialkoxynonane compound (7) or the 9,9-dialkoxynonyltriarylphosphonium halide compound (9) in view of the reactivity.

Wittig Reaction

An amount of the triarylphosphonium dialkoxyalkylide compound (4) is preferably from 1.0 to 4.0 mol, more preferably from 1.0 to 2.0 mol, per mol of 4-penten-2-ynal (3) in view of the reactivity.

A solvent may be used in a Wittig reaction, if necessary.

Examples of the solvent include ether solvents such as tetrahydrofuran, diethyl ether, dibutyl ether, 4-methyltetrahydropyran, cyclopentyl methyl ether, and 1,4-dioxane; hydrocarbon solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform. Ether solvents such as tetrahydrofuran and polar solvents such as acetonitrile, N,N-dimethylformamide, and N,N-dimethylacetamide are preferred in view of the reactivity.

The solvent may be used either alone or in combination thereof. The solvent may be commercially available one.

An amount of the solvent is preferably from 50 to 5000 g per mol of 4-penten-2-ynal (3) in view of the reactivity.

An optimum temperature in a Wittig reaction varies, depending on the solvent used, and is preferably from −78 to 40° C. In a case where a Wittig reaction is carried out in preference to Z, the temperature is preferably −78 to 10° C. In a case where a Wittig reaction is carried out in preference to E, the temperature is preferably −78 to −40° C. Then, an intermediate product is allowed to react in a modified Schlosser condition where the intermediate product is treated with a strong base such as phenyl lithium.

A reaction time in the Wittig reaction varies, depending on a production scale, and is preferably from more than 0 (>0) to 50 hours.

Preparation of a dialkoxyalkadienyne compound (1-1) by an acetal exchange reaction The dialkoxyalkadieuyne compound (1-1) of the following general formula (1-1) is obtained by a process of an acetal exchange reaction of the aforesaid dialkoxyalkadienyne compound (1), as shown in the following chemical reaction formula.

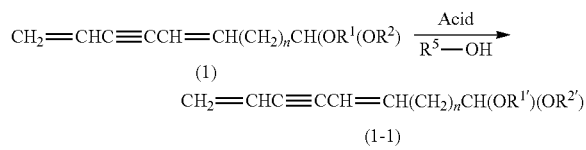

The acetal exchange reaction may be carried out with, for instance, an alcohol and an acid.

Examples of the acid include inorganic acids such as hydrochloric acid and hydrobromic acid organic acids such as p-toluenesulfonic acid, benzenesulfonic acid, trifluoroacetic acid, acetic acid, formic acid and oxalic acid; and iodotrimethylsilane and titanium tetrachloride, p-Toluenesulfonic acid and benzenesulfonic acid are preferred in view of foe reactivity.

The acid may alone or in combination thereof. The acid may be commercially available one.

An amount of foe acid is preferably 0.001 to 10.0 mol per mol of the dialkoxyalkadienyne compound (1).

The alcohol is represented by the following general formula (10).

$R^5$ represents a monovalent hydrocarbon group having 1 to 15 carbon atoms, preferably 1 to 5 carbon atoms.

Specific examples of foe monovalent hydrocarbon group leaving 1 to 15 carbon atoms are same as the specific examples of the monovalent hydrocarbon groups for $R^1$ and $R^2$ in the dialkoxyalkadienyne compound (1).

Specific examples of the alcohols include linear saturated alcohols such as methanol, ethanol, propanol, and 1-butanol; branched saturated alcohols such as isopropanol 2-methylpropanol and 2-methylbutanol; linear unsaturated alcohols such as 2-propenol; branched unsaturated alcohols such as 2-methyl-2-propenol; cyclic saturated alcohols such as cyclohexanol; and isomers thereof. A part of the hydrogen atoms of these hydrocarbon groups may be substituted with a methyl group or ail ethyl group.

The alcohols may used other alone or in combination thereof. The alcohol may be commercially available one.

An amount of the alcohol is preferably 2.0 to 500 mol per mol of foe dialkoxyalkadienyne compound (1).

A reaction temperature in the acetal exchange reaction is preferably 0 to 180° C., more preferably 30 to 80° C., in view of the reactivity.

A reaction time in the acetal exchange reaction varies, depending on a solvent used or a production scale, and is preferably 1 to 55 hours in view of the reactivity.

$R^{1'}$ and $R^{2'}$ in the dialkoxyalkadienyne compound (1-1) after the acetal exchange reaction are, independently of each other, a monovalent hydrocarbon group having 1 to 15 carbon atoms, preferably 1 to 8, mere preferably 1 to 4, or $R^{1'}$ and $R^{2'}$ may bonded to each other to form a divalent hydrocarbon group, $R^{1'}$-$R^{2'}$, having 2 to 10 carbon atoms, and n represents an integer of 0 to 11. The $R^{1'}$ of the dialkoxyalkadienyne compound (1-1) may be same as the group $R^1$ of the dialkoxyalkadienyne compound (1) before the acetal exchange reaction, or same as the group $R^5$ after the acetal exchange reaction. Meanwhile, the group $R^{2'}$ of the dialkoxyalkadienyne compound (1-1) may be same as the group $R^2$ of the dialkoxyalkadienyne compound (1) before the acetal exchange reaction, or same as the group $R^5$ after the acetal exchange reaction. However, a combination of $R^{1'}$ and $R^{2'}$ shall not be same as a combination of $R^1$ and $R^2$ before the acetal exchange reaction. The number n of the dialkoxyalkadieuyne compound (1-1) is the same as the number n of the dialkoxyalkadienyne compound (1) before the acetal exchange reaction.

Preparation of the Dialkoxyalkadienyne Compound (1-2) by Acetalization

The dialkoxyalkadienyne compound of the following general formula (1-2) may be obtained by acetalization of the dienynal compound of the following general formula (2), as shown in the following chemical reaction formula.

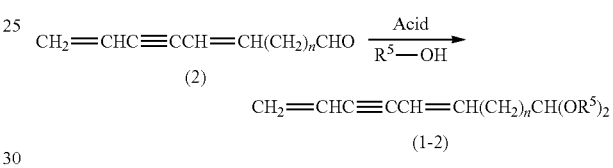

The acetalization reaction may be carried out with, for example, an alcohol and an acid.

Examples of the acid include inorganic acids such as hydrochloric acid and hydrobromic acid, and organic acids such as p-toluenesulfonic acid, benzenesulfonic acid, trifluoroacetic acid, acetic acid formic acid and oxalic acid; and iodotrimethylsilane and titanium tetrachloride, p-Toluenesulfinic acid and benzenesulfonic acid are preferred in view of the reactivity.

The acid may be used either alone or in combination thereof. The acid may be commercially available one.

An amount of the acid is preferably 0.0001 to 10.0 mol per mol of the dienynal compound (2).

The alcohol is as defined in the aforesaid section "Production of the dialkoxyalkadienyne compound (1-1) by acetal exchange reaction" and is represented by the aforesaid general formula (10).

Specific examples of the alcohol are same as those mentioned in the aforesaid section "Production of the dialkoxyalkadienyne compound (1-1) by acetal exchange reaction".

The alcohol may be used either alone or in combination thereof. The alcohol may be commercially available one.

An amount of the alcohol is preferably 2.0 to 500 mol per mol of the dienynal compound (2).

An orthoformate ester compound may be used, if needed, to remove water formed in the acetalization reaction.

Examples of the orthoformate compound include methyl orthoformate, ethyl orthoformate, propyl orthoformate, butyl orthoformate, and pentyl orthoformate.

The orthoformate compound may be used either alone or in combination thereof. The orthoformate compound may be commercially available one.

A reaction temperature in the acetalization is preferably −20 to 180° C., more preferably 0 to 80° C., in view of the reactivity.

A reaction time in the acetalization varies, depending on a solvent used or a production scale, and is preferably 1 to 55 hours in view of foe reactivity.

The dienynal compound (2) described above may be prepared by hydrolysis of the aforesaid dialkoxyalkadienyne compound (1) to obtain the dienynal compound (2), as shown in the chemical reaction formula below.

$$CH_2{=}CHC{\equiv}CCH{=}CH(CH_2)_nCH(OR^1)(OR^2) \xrightarrow[\text{Water}]{\text{Acid}}$$
(1)
$$CH_2{=}CHC{\equiv}CCH{=}CH(CH_2)_nCHO$$
(2)

The dialkoxyalkadienyne compound (1) may be used either alone or in combination of thereof if necessary, in the hydrolysis.

Far instance, a mixture of the 14,14-dialkoxy-(5Z)-1,5-tetradecadien-3-yne compound and the 14,14-dialkoxy-(5E)-1,5-tetradecadien-3-yne compound may be used to obtain a mixture of (9Z)-9,13-tetradecadien-11-ynal and (9E)-9,13-tetradecadien-11-ynal.

The hydrolysis may be carried out using, for example, an acid or water.

Examples of the acid include inorganic acids such as hydrochloric acid and hydrobromic acid, p-toluenesulfonic acid, benzenesulfonic acid, trifluoroacetic acid, acetic acid, formic acid and oxalic acid; and iodotrimethylsilane and titanium tetrachloride. Acetic acid, formic acid or oxalic acid is preferred in view of foe reactivity.

The acid may be used either alone or in combination thereof. The acid may be commercially available one.

An amount of the acid is preferably 0.01 to 10.0 mol per mol of the dialkoxyalkadienyne compound (1).

An amount of water is preferably 18 to 3000 g per mol of the dialkoxyalkadienyne compound (1) in view of the reactivity.

A solvent may be used in the hydrolysis, if necessary, together with the aforesaid acid or water.

Examples of the solvent include hydrocarbon solvents such as toluene, xylene, hexane, heptane, benzene, and cumene; ether solvents such as tetrahydrofuran, diethyl ether, dibutyl ether, 4-methyltetrahydropyran, cycloheptylmethyl ether, and 1,4-dioxane; polar solvents such as N,N-dimethylfomamide, N,N-dimethylacetamide, N-methylpyrrolidone, dimethyl sulfoxide, acetonitrile, acetone, γ-butyrolactone, dichloromethane and chloroform; and alcohols such as methanol and ethanol.

The solvent may be used either alone or in combination thereof. The solvent may be commercially available one.

An optimum solvent varies, depending on an acid used. For instance, when oxalic acid is used as the acid, the solvent is preferably tetrahydrofuran, acetone and γ-butyrolactone in view of the reactivity.

An amount of the solvent is preferably from 0 to 3,000 g per mol of the dialkoxyalkadienyne (1) in view of the reactivity.

A reaction temperature in the hydrolysis varies, depending on an acid or solvent used, and is preferably from 5 to 180° C. in view of the reactivity.

A reaction time in the hydrolysis varies, depending on a solvent used or a production scale, and is preferably from 1 to 55 hours in view of the reactivity.

"n" in the dienynal compound (2) represents an integer of 0 to 11, preferably 2 to 9.

The dienynal compound (2) is (Z)-dienynal compound of the following general formula (2-Z), or (E)-dienynal confound of the following general formula (2-E), mixtures thereof.

Examples of the dienynal compound (2) include 2,6-heptadien-4-ynal (n=0), 3,7-octadien-5-ynal (n=1), 4,8-nonadien-6-ynal (n=2), 5,9-decadien-7-ynal (n=3), 6,10-undecadien-8-ynal (n=4), 7,11-dodecadien-9-ynal (n=5), 8,12-decadien-10-ynal (n=6), 9,13-tetradecadien-11-ynal (n=7), 10,14-pentadecadien-12-ynal (n=8), 11,15-hexadecadien-13-ynal (n=9), 12,16-hexadecadien-14-ynal (n=10), and 13,17-hexadecadien-15-ynal (n=11).

Specific examples of 2,6-heptadien-4-ynal (n=0) include (2Z)-2,6-heptadien-4-ynal and (2E)-2,6-heptadien-4-ynal.

Specific examples of 3,7-octadien-5-ynal (n=1) include (3Z)-3,7-octadien-5-ynal and (3E)-3,7-octadien-5-ynal.

Specific examples of 4,8-nonadien-6-ynal (n=2) include (4Z)-4,8-nonadien-6-ynal and (4E)-4,8-nonadien-6-ynal.

Specific examples of 5,9-decadien-7-ynal (n=3) include (5Z)-5,9-decadien-7-ynal and (5E)-5,9-decadien-7-ynal.

Specific examples of 6,10-undecadien-8-ynal (n=4) include (6Z)-6,10-undecadien-8-ynal and (6E)-6,10-undecadien-8-ynal.

Specific examples of 7,11-dodecadien-9-ynal (n=5) include (7Z)-7,11-dodecadien-9-ynal and (7E)-7,11-dodecadien-9-ynal.

Specific examples of 8,12-decadien-10-ynal (n=6) include (8Z)-8,12-tridecadien-10-ynal and (8E)-8,12-decadien-10-ynal.

Specific examples of 9,13-tetradecadien-11-ynal (n=7) include (9Z)-9,13-tetradecadien-11-ynal and (9E)-9,13-tetradecadien-11-ynal.

Specific examples of 10,14-pentadecadien-12-ynal (n=8) include (10Z)-10,14-pentadecadien-12-ynal and (10E)-10,14-pentadecadien-12-ynal.

Specific examples of 11,15-hexadecadien-1,3-ynal (n=9) include (11Z)-11,15-hexadecadien-13-ynal and (11E)-11,15-hexadecadien-1,3-ynal.

Specific examples of 12,16-hexadecadien-14-ynal (n=10) include (12Z)-12,16-hexadecadien-14-ynal and (12E)-12,16-hexadecadien-14-ynal.

Specific examples of 13,17-hexadecadien-15-ynal (n=11) include (13Z)-13,17-hexadecadien-15-ynal and (13E)-13,17-hexadecadien-15-ynal.

EXAMPLES

The present invention will be further described with reference to the following Examples. It should be understood that the present invention is not limited to or by the Examples.

The term "purity" as used herein means an area percentage in gas chromatography (GC), unless otherwise specified.

The term "production ratio" means a ratio of area percentages in GC. The yield is calculated from the area percentages in GC.

In the Examples, monitoring of the reactions was aimed out in the following GC conditions.

GC conditions: Capillary gas chromatograph GC-2014, ex Shimadzu Corporation; column: DB-5, 0.25 mm×0.25 mmφ×30 m; carrier gas: He (1.55 mL/min); detector FID; column temperature: 150° C., elevated by 5° C./min, up to 230° C.

The yield was calculated according to the following equation in consideration of purities (% GC) of a starting material and a product.

Yield (%)={[(weight of a product obtained by a reaction×% GC)/molecular weight of a product]÷[(weight of a starting material in a reaction×% GC)/molecular weight of a starting material]}×100

Example 1

Preparation of 5,5-diethoxy-1-penten-3-yne (5: $R^3$=Et, $R^4$=Et)

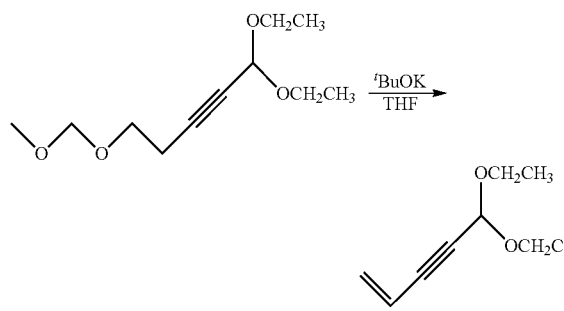

Potassium t-butoxide (tBuOK) (40239 g, 3.59 mol) and tetrahydrofuran (THF) (1856.64 g) were placed in a reactor at room temperature and stirred at 10 to 15° C. for 28 minutes. Then, 1,1-diethoxy-5-(methoxymethoxy)-2-pentyne (6: $R^3$=Et, $R^4$=Et; Z=CH$_3$OCH$_2$O) (704.18 g, 326 mol, purity: 100%) was added dropwise to the reactor at 10 to 15° C. After the completion of the dropwise addition, the reaction mixture was stirred at 10 to 20° C. for 5.5 hours. Next, water (1953.60 g) was added to the reaction mixture, followed by phase separation and removal of the aqueous phase to obtain the organic phase. Then, the organic phase was concentrated at a reduced pressure and the residue was subjected to distillation at a reduced pressure (51.3 to 57.9° C./3.0 mmHg (0.40 kPa)) to obtain 5,5-diethoxy-1-penten-3-yne (5: $R^3$=Et, $R^4$=Et) (436.26 g, 2.78 mol, purity: 98.41%) in a yield of 85.52%.

The following is the spectrum data of 5,5-diethoxy-1-penten-3-yne (5: $R^3$=Et, $R^4$=Et) tins produced.

[Nuclear magnetic resonance spectrum]$^1$H-NMR (500 MHz, CDCl$_3$): δ 1.22 (6H, t, 7.1 Hz), 3.58 (2H, dq, J=6.9 Hz, 7.8 Hz), 3.73 (2H, dq, J=6.9 Hz, 7.9 Hz), 5.36 (1H, J=1.6 Hz), 5.52 (1H, dd, J=11.0 Hz, 2.3 Hz), 5.69 (1H, dd, J=17.6 Hz, 2.3 Hz), 5.81 (1H, ddd, J=17.8 Hz, 10.9 Hz, 1.5 Hz), $^{13}$C-NMR (125 MHZ, CDCl$_3$): δ 15.01, 60.81, 83.76, 84.89, 91.57, 116.04, 128.48.

[Mass spectrum] EI-Mass spectrum (70 eV): m/z 153 (M$^+$-1), 125, 109, 81, 63, 53.

[Infrared absorption spectrum] (NaCl): νmax 2977, 2886, 1355, 1328, 1162, 1091, 1054, 1012.

Example 2

Preparation of 5,5-diethoxy-1-penten-3-yne (5: $R^3$=Et, $R^4$=Et)

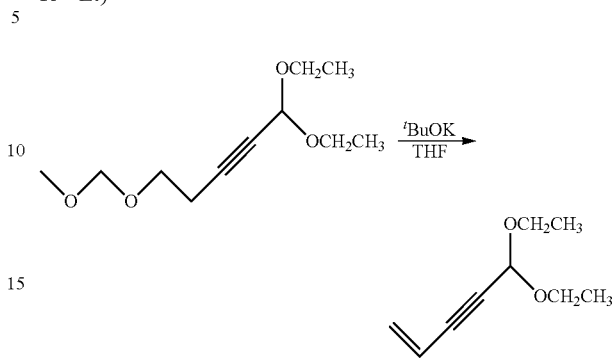

Potassium t-butoxide (17.08 g, 0.15 mol) and N,N-dimethylfomamide (DMF) (78.92 g) were placed in a reactor at room temperature and stirred at from 10 to 15° C. for 40 minutes. Then, 1,1-diethoxy-5-(methoxymethoxy)-2-pentyne (6: $R^3$=Et, $R^4$=Et, Z=CH$_3$OCH$_2$O) (30.00 g, 0.14 mol, purity: 99.80%) was added dropwise to the reactor at 10 to 15° C. After the completion of the dropwise addition, the reaction mixture was stirred at from 10 to 20° C. for 3 hours. Next, water (83.04 g) was added to the reaction mixture, followed by phase separation and removal of the aqueous phase to obtain the organic phase. Then, the organic phase was concentrated at a reduced pressure and the residue was subjected to distillation at a reduced pressure (51.3 to 57.9° C./3.0 mmHg (0.40 kPa)) to obtain 5,5-diethoxy-1-penten-3-yne (5: $R^3$=Et, $R^4$=Et) (15.42 g, 0.072 mol, purity: 70.41%) in a yield of 50.87%.

The spectra data of 5,5-diethoxy-1-penten-3-yne (5: $R^3$=Et, $R^4$=Et) thus obtained were same as those in Example 1.

Example 3

Preparation of 5,5-diethoxy-1-penten-3-yne (5: $R^3$=Et, $R^4$=Et)

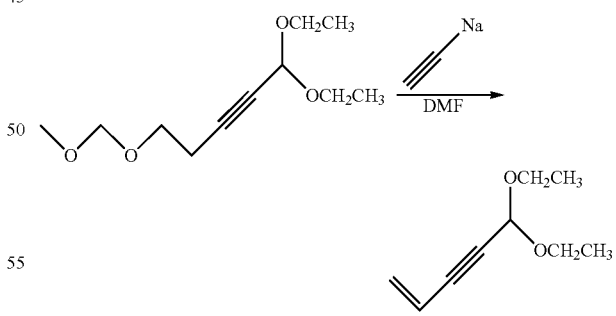

Sodium acetylide (731 g 0.15 mol) and N,N-dimethylformamide (78.92 g) were placed in a reactor at room temperature and stirred at from 10 to 15° C. for 40 minutes. Then, 1,1-diethoxy-5-(methoxymethoxy)-2-pentyne (6: $R^3$=Et, $R^4$=Et; Z=CH$_3$OCH$_2$O) (30.00 g, 0.14 mol purity: 99.80%) was added dropwise to the reactor at 10 to 15° C. After the completion of the dropwise addition, flic reaction mixture was stirred at from 10 to 20° C. for 3 hours, and further at 60° C. for 2.5 hours. Next, water (83.04 g) was added to the reaction mixture, followed by phase separation and removal of the aqueous phase to obtain the organic phase. Then, the organic phase was concentrated at a reduced pressure and the residue was subjected to distillation at a reduced pressure (513 to 57.9° C./3.0 mmHg (0.40 kPa)) to obtain 5,5-diethoxy-1-penten-3-yne (5: $R^3$=Et, $R^4$=Et) (3621 g, 0.026 mol, purity: 10.89%) in a yield of 18.48%.

The plectra data of 5,5-diethoxy-1-penten-3-yne (5: $R^3$=Et, $R^4$=Et) thus obtained were same as those in Example 1.

Example 4

Preparation of 5,5-dimethoxy-1-penten-3-yne (5: $R^3$=Me, $R^4$=Me)

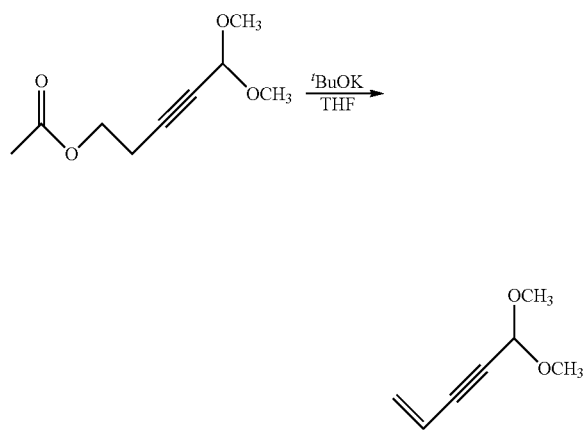

Potassium t-butoxide (23.19 g, 021 mol) and tetrahydrofuran (107.14 g) were placed in a reactor at room temperature and stirred at from 10 to 15° C. for 25 minutes. Then, 1,1-dimethoxy-5-acetyloxy-2-pentyne (6: $R^3$=Me, $R^4$=Me; Z=$CH_3C$(=O)—C)) (34.99 g, 0.19 mol) was added dropwise to the reactor at 10 to 15° C. After the completion of foe dropwise addition, the reaction mixture was stirred at from 10 to 20° C. for 1 hour. Next, water (112.74 g) was added to the reaction mixture, followed by phase separation and removal of the aqueous phase to obtain the organic phase. Then, the organic phase was concentrated at a reduced pressure and the residue was subjected to distillation at a reduced pressure (692 to 71.1° C./25.0 mmHg (3.33 kPa)) to obtain 5,5-dimethoxy-1-penten-3-yne (5: $R^3$=Me, $R^4$=Me) (20.73 g. 0.16 mol) in a yield of 87.44%.

The following is foe spectrum data of 5,5-dimethoxy-1-penten-3-yne (5: $R^3$=Me, $R^4$=Me) thus produced.

[Nuclear magnetic resonance spectrum] $^1$H-NMR (500 MHz, CDCl$_3$): δ 3.37 (6H, s), 5.24 (1H, J=1.1 Hz), 5.55 (1H, dd, J=23 Hz, 11.1 Hz), 5.71 (1H, dd, J=2.3 Hz, 17.7 Hz), 5.82 (1H, ddd, J=1.2 Hz, 10.9 Hz, 17.9 Hz); $^{13}$C-NMR (125 MHz, CDCl$_3$): δ 52.42, 83.96, 84.30, 93.30, 115.82, 128.75.

[Mass spectrum] H-Mass spectrum (70 eV): m/z 125 (MM), 111,95,80,65,52.

[Infrared absorption spectrum] (NaCl): νmax 2938, 2905, 2831, 2230, 1603, 1358, 1343, 1192, 1162, 1099, 1056, 963, 901.

Example 5

Preparation of 5,5-dimethoxy-1-penten-3-yne (5: $R^3$=Me, $R^4$=Me)

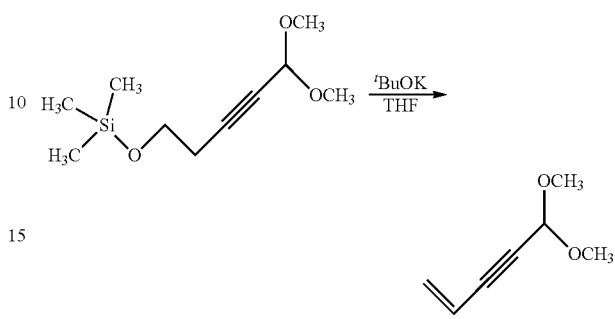

Potassium t-butoxide (23.61 g, 0.21 mol) and tetrahydrofuran (109.08 g) were traced in a reactor at room temperature and stirred at from 10 to 15° C. for 17 minutes. Then, 1,1-dimethoxy-5-trimethylsilyloxy-2-pentyne (6: $R^3$=Me, $R^4$=Me; Z=(CH$_3$)$_3$SiO) (41.39 g, 0.19 mol) was added dropwise to the reactor at from 10 to 15° C. After the completion of the dropwise addition, the reaction mixture was stirred at from 10 to 20° C. for 1.5 hours. Next, water (114.78 g) was added to the reaction mixture, followed by phase separation and removal of the aqueous phase to obtain the organic phase. Then, the organic phase was concentrated at a reduced pressure and the residue was subjected to distillation at a reduced pressure (692 to 71.1° C./25.0 mmHg (3.33 kPa)) to obtain 5,5-dimethoxy-1-penten-3-yne (5: $R^3$=Me, $R^4$=Me) (13.02 g, 0.10 mol) in a yield of 53.93%.

The spectra data of 5,5-dimethoxy-1-penten-3-yne (5: $R^3$=Me, $R^4$=Me) thus obtained were same as those in Example 4.

Example 6

Preparation of 5,5-dimethoxy-1-penten-3-yne (5: $R^3$=Me, $R^4$=Me)

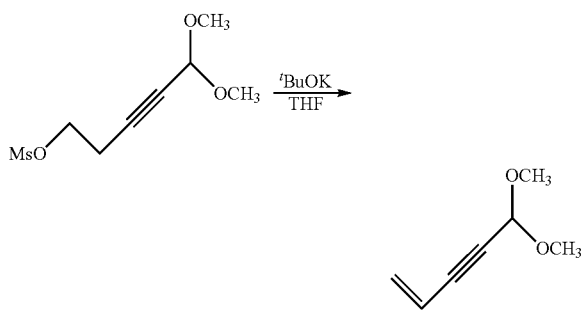

Potassium t-butoxide (23.96 g, 0.21 mol) and tetrahydrofuran (110.68 g) were placed in a reactor at room temperature and stirred at from 10 to 15° C. for 21 minutes. Then, 1,1-dimethoxy-5-methanesulfonyloxy-2-pentyne (6: $R^3$=Me, $R^4$=Me; Z=OMs (i.e., OSO$_2$CH$_3$)) (43.14 g, 0.19 mol) was added dropwise to the reactor at from 10 to 15° C. After the completion of the dropwise addition, the reaction mixture was stirred at from 10 to 20° C. for 1.5 hours. Next, water (116.46 g) was added to the reaction mixture, followed by phase separation and removal of the aqueous phase to obtain the organic phase. Then, the organic phase was concentrated at a reduced pressure and the residue was subjected to distillation at a reduced pressure (69.2 to 71.1° C./25.0 mmHg (3.33 kPa)) to obtain 5,5-dimethoxy-1-penten-3-yne (5: $R^3$=Me, $R^4$=Me) (14.22 g, 0.11 mol) in a yield of 58.05%.

The spectra data of 5,5-dimethoxy-1-penten-3-yne (5: $R^3$=Me, $R^4$=Me) thus obtained were same as those in Example 4.

Example 7

Preparation of 4-penten-2-ynal (3)

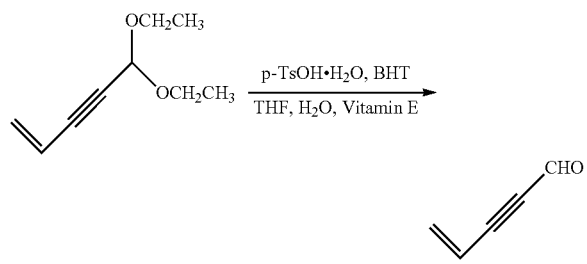

5,5-Diethoxy-1-penten-3-yne (5: $R^3$=Et $R^4$=Et) (46.26 g. 0.30 mol) which had been prepared as in Example 1 and purified, vitamin E (0.20 g), dibutylhydroxytoluene (BHT) (020 g), tetrahydrofuran (150.00 g) and water (150.00 g) were placed in a reactor at room temperature and stoned at from 20 to 30° C. for 5 minutes. Then, p-toluenesulfonic acid monohydrate (p-TsOH·$H_2O$) (2.91 g, 0.015 mol) was added to the reactor at from 20 to 30° C. and stirred at from 60 to 65° C. for 3 hours. Next, sodium hydrogen carbonate (2.52 g) and toluene (27231 g: including 40 g of toluene for taking up sodium hydrogen carbonate from a vessel) were added to the reaction mixture, followed by phase separation and removal of the aqueous phase to obtain the organic phase. Then, the organic phase was concentrated at a reduced pressure to obtain 4-penten-2-ynal (3) (17.93 g, 0.22 mol) in a mixed solvent of toluene (234.36 g) and tetrahydrofuran (93.53 g) in a yield of 74.63%. The amounts of toluene and tetrahydrofuran in the mixture were determined by GC and NMR.

The following is the spectrum data of 4-penten-2-ynal (3) this produced.

[Nuclear magnetic resonance spectrum]$^1$H-NMR (500 MHz, $CDCl_3$): δ 9.35 (1H, d, J=0.7 Hz), 6.08 (1H, dd, J=172 Hz, 2.3 Hz), 6.01 (1H, ddd, J=17.4 Hz, 10.9 Hz, 0.7 Hz), 5.91 (1H, dd, J=10.9 Hz, 23 Hz); $^{13}$C-NMR (125 MHz, $CDCl_3$): δ 88.28, 93.02, 114.75, 134.25, 176.70

[Mass spectrum] EI-Mass spectrum (70 eV): m/z 80 (M$^+$), 61.52

[Mated absorption spectrum] (NaCl): vmax 2977, 2873, 2210, 2172, 1664, 1162, 1080, 1035, 972, 947, 798

Example 8

Preparation of 14,14-diethoxy-1,5-tetradecadien-3-yne (1: $R^1$=Et, $R^2$=Et; n=7)

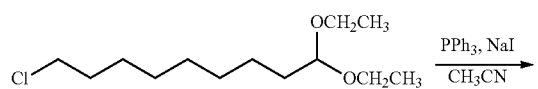

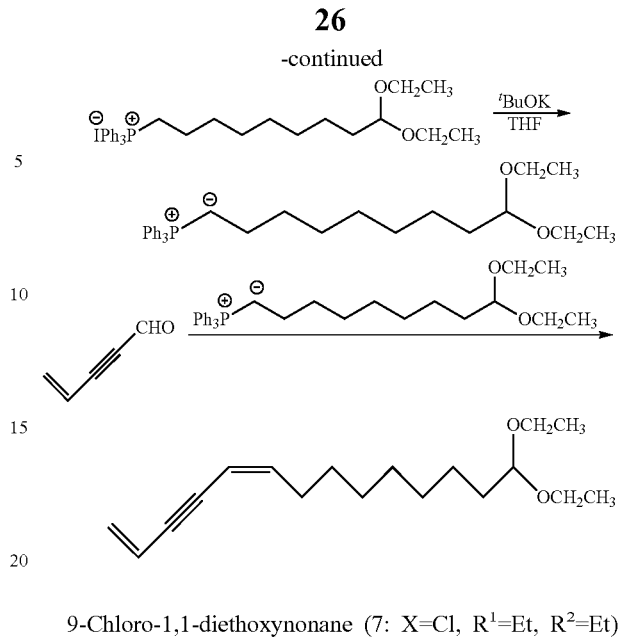

9-Chloro-1,1-diethoxynonane (7: X=Cl, $R^1$=Et, $R^2$=Et) (67.72 g, 0.27 mol), triphenylphosphine (8: Ar=Ph) (63.74 g, 0.27 mol) sodium iodide (40.47 g, 0.30 mol), potassium carbonate (2.07 g, 0.015 mol), and acetonitrile (173.20 g) were placed in a reactor at room temperature and stirred at from 75 to 85° C. for 15 hours to obtain 9,9-diethoxynonyltriphenylphosphonium iodide (9: Y=I, Ar=Ph; $R^1$=Et, $R^2$=Et). Then tetrahydrofuran (311.53 g) was added dropwise to the reactor at 30 to 40° C. After the completion of the dropwise addition, the reaction mixture was cooled to −5 to 10° C. Next potassium t-butoxide (27.27 g, 024 mol) was added and stirred for 1 hour to obtain triphenylphosphonium 9,9-diethoxynonylide (4: Ar=Ph; $R^1$=Et $R^2$=Et).

Next 4-penten-2-ynal (3) (16.14 g, 020 mol) which had been prepared as in Example 7 in a mixed liquid of toluene (220.99 g) and tetrahydrofuran (78.56 g) was added dropwise to the reactor at from −5 to 5° C. After the completion of the dropwise addition, the reaction mixture was stirred at from 20 to 30° C. for 2.5 hours. Next, a solution of sodium chloride (45.47 g) in water (454.65 g) was added to the reaction mixture, followed by phase separation and removal of the aqueous phase to obtain the organic phase. Then, the organic phase was concentrated at a reduced pressure to obtain a crude product, 14,14-diethoxy-1,5-tetradecadien-3-yne (1: $R^1$=Et, $R^2$=Et; n=7), (65.39 g, 0.18 mol, purity: 77.92%, E/Z=24/76) in a crude yield of 83.18%. The crude product contained toluene, triphenylphosphine, and triphenylphosphine oxide as impurities.

The following is the spectrum data of 14,14-diethoxy-1,5-tetradecadien-3-yne (1: $R^1$=Et, $R^2$=Et; n=7) thus produced.

[Nuclear magnetic resonance spectrum]$^1$H-NMR (500 MHz, $CDCl_3$): δ 1.19 (6H, t, J=7.1 Hz), 125-1.44 (10H, m), 1.56-1.62 (2H, m), 2.30 (2H, ddt, J=1.1 Hz, 7.3 Hz, 7.3 Hz), 3.47 (2H, dq, J=6.9 Hz, 7.8 Hz), 3.62 (2H, dq J=6.9 Hz, 7.8 Hz), 4.46 (1H, t, J=5.9 Hz), 5.44 (1H, dd, J=11.1 Hz, 2.3 Hz), 5.53-5.57 (1H, m), 5.60 (1H, dd, J=17.6 Hz, 2.3 Hz), 5.87-5.97 (2H, m); $^{13}$C-NMR (125 MHz, $CDCl_3$): δ 15.32, 24.70, 28.75, 29.01, 29.31, 29.37, 30.22, 33.55, 60.77, 87.02, 92.12, 102.92, 108.79, 117.39, 125.98, 144.35.

[Mass spectrum] EI-Mass spectrum (70 eV): m/z 278 (M$^+$), 233, 189, 175, 161, 145, 131, 117, 103, 75, 57.

Example 9

Preparation of 9,13-tetradecadien-11-ynal (2: n=7)

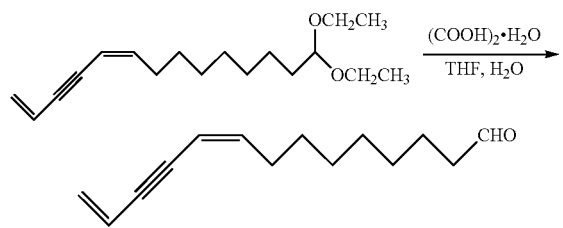

Subsequently, the crude product obtained in Example 8, 14,14-diethoxy-1,5-tetradecadien-3-yne (1: R$^1$=Et, R$^2$=Et; n=7) (65.39 g, 0.18 mol purity: 77.92%, E/Z=24/76), oxalic acid dihydrate (6921 g, 0.55 mol), tetrahydrofuran (183.00 g), and pure water (183.00 g) were added to a reactor at room temperature and stirred at from 60 to 65° C. for 3.5 hours. Then, the reaction mixture was cooled to 50° C., and hexane (53.82 g) was added, and the reaction mixture was stirred for 30 minutes. After completion of the stirring, the reaction mixture was allowed to stand for phase separation, followed by removal of the aqueous phase to obtain the organic phase. Then, the organic phase was concentrated at a reduced pressure and the residue was subjected to distillation at a reduced pressure (125.1 to 133.1° C./3.0 mmHg (0.40 kPa)) to obtain 9,13-tetradecadien-11-ynal (2: n=7) (28.97 g, 0.13 mol purity: 93.52%, E/Z=24/76) in an overall yield of Examples 8 and 9 of 66.30%.

The following is the spectrum data of 9,13-tetradecadien-11-ynal (2: n=7) thus produced.

[Nuclear magnetic resonance spectrum]$^1$H-NMR (500 MHz, CDCl$_3$): δ 1.27-1.35 (6H, m), 1.40 (2H, hr. quint J=6.5 Hz), 1.61 (2H, br. quint, J=6.9 Hz), 230 (2H, ddt, J=1.5 Hz, 7.3 Hz, 7.3 Hz), 2.40 (2H, dt, J=1.9 Hz, 7.3 Hz), 5.44 (1H, dd, J=112 Hz, 19 Hz), 5.55 (1H, br.dd, J=10.7 Hz, 1.9 Hz), 5.60 (1H, dd, J=17.6 Hz, 1.9 Hz), 5.86-5.97 (2H, m), 9.75 (1H, t, J=1.9 Hz); $^{13}$C-NMR (125 MHz, CDCl$_3$): δ 21.99, 28.63, 28.80, 29.01, 29.05, 30.14, 43.84, 86.98, 92.16, 108.91, 117.36, 126.03, 144.18, 202.80.

[Mass spectrum] H-Mass spectrum (70 eV): m/z 204 (M$^+$), 175, 161, 147, 133, 119, 105, 91, 78, 65, 53.

[Infrared absorption spectrum] (NaCl): vmax 2929, 2856, 1725, 1464, 1413, 1392, 972, 918, 739.

Example 10

Preparation of 9,13-tetradecadien-11-ynal (2: n=7)

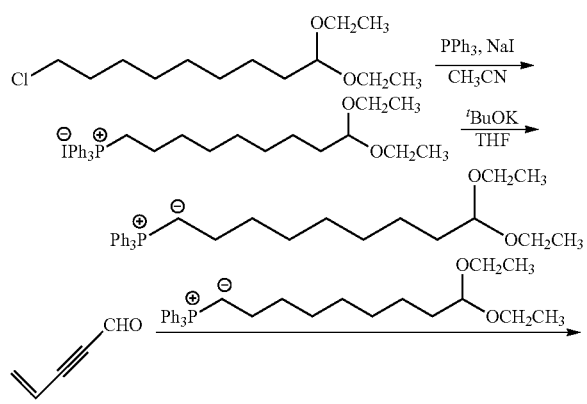

9-Chloro-1,1-diethoxynonane (7: X=Cl; R$^1$=Et, R$^2$=Et) (90.29 g, 0.36 mol), triphenylphosphine (8: Ar=Ph) (94.65 g, 0.36 mol), sodium iodide (58.46 g, 0.39 mol), potassium carbonate (2.90 g, 0.021 mol), and acetonitrile (192.45 g) were placed in a reactor at room temperature and stirred at from 75 to 85° C. for 15 hours to obtain 9,9-diethoxynonyltriphenylphosphonium iodide (9: Y=I; Ar=Ph; R$^1$=Et, R$^2$=Et). Then, tetrahydrofuran (346.14 g) was added dropwise to the reactor at 30 to 40° C. After the completion of the dropwise addition, the reaction mixture was cooled to −5 to 10° C. Next potassium t-butoxide (38.71 g, 0.35 mol) was added and stirred for 1 hour to obtain triphenylphosphonium 9,9-diethoxynonylide (4: Ar=Ph; R$^1$=Et, R$^2$=Et).

Next 4-penten-2-ynal (3) (16.14 g, 020 mol) which had been prepared as in Example 7 in a mixed liquid of toluene (220.99 g) and tetrahydrofuran (78.56 g) was added dropwise to tire reactor at from −5 to 5° C. After the completion of tire dropwise addition, the reaction mixture was stirred at from 20 to 30° C. for 2 hours. Next, a solution of sodium chloride (45.47 g) in water (454.65 g) was added to tire reaction mixture, followed by phase separation and removal of the aqueous phase to obtain the organic phase. Then, the organic phase was concentrated at a reduced pressure to obtain a crude product, 14,14-diethoxy-1,5-tetradecadien-3-yne (1: R$^1$=Et, R$^2$=Et; n=7), (74.22 g, 0.18 mol, purity: 68.06%, E/Z=26/74) in a crude yield of 90.02%. The crude product contained toluene, triphenylphosphine, and triphenylphosphine oxide as impurities.

Subsequently, the crude product thus obtained, 14,14-diethoxy-1,5-tetradecadien-3-yne (1: R$^1$=Et, R$^2$=ET, n=7) (74.22 g, 0.18 mol, purity: 68.06%, E/Z=26/74), oxalic acid dihydrate (68.61 g, 0.54 mol), tetrahydrofuran (181.40 g), and pure water (181.40 g) were added to a reactor at room temperature and stirred at from 60 to 65° C. for 4 hours. Then, the reaction mixture was cooled to 50° C., and hexane (53.35 g) was added, and the reaction mixture was stirred for 30 minutes. After completion of the stirring, the reaction mixture was allowed to stand for phase separation, followed by removal of the aqueous phase to obtain the organic phase. Thai, the organic phase was concentrated at a reduced pressure and the residue was subjected to distillation at a reduced pressure (125.1 to 133.1° C./3.0 mmHg (0.40 kPa)) to obtain 9,13-tetradecadien-11-ynal (2: n=7) (31.40 g 0.15 mol, purity. 96.03%, E/Z=25/75) in an overall yield of the 2 steps of 73.25%.

The spectra data of 9,13-tetradecadien-11-ynal (2: n=7) thus obtained were same as those in Example 9.

Example 11

Preparation of 9,13-tetradecadien-11-ynal (2: n=7)

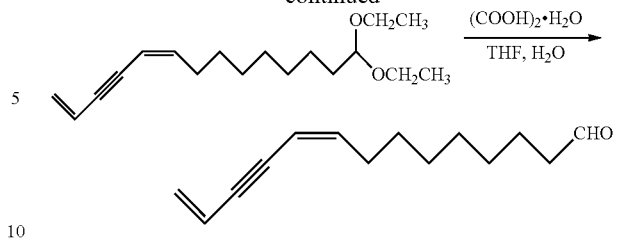

-continued

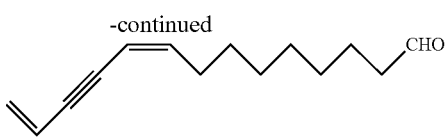

A product prepared as in Example 8 and purified, 14,14-diethoxy-1,5-tetradecadien-3-yne (1:R¹=Et, R²=Et; n=7) (16.06 g, 0.058 mol, E/Z=1/99), oxalic acid dihydrate (21.85 g, 0.17 mol), tetrahydrofuran (57.76 g), and pure water (57.76 g) were added to a reactor at room temperature and stirred at from 60 to 65° C. for 4 hours. Then, the reaction mixture was cooled to 50° C., and hexane (53.82 g) was added, and the reaction mixture was stirred for 30 minutes. After completion of the stirring, the reaction mixture was allowed to stand for phase separation, followed by removal of the aqueous phase to obtain the organic phase. Then, the organic phase was concentrated at a reduced pressure and the residue was subjected to distillation at a reduced pressure (125.1 to 133.1° C./3.0 mmHg (0.40 kPa)) to obtain 9,13-tetradecadien-11-ynal (2: n=7) (11.43 g, 0.056 mol, E/Z=1/99) in a yield of 96.82%.

The spectra data of 9,13-tetradecadien-11-ynal (2: n=7) thus obtained woe same as those in Example 9.

Example 12

Preparation of 9,9-dimethoxy-1,5-nonadien-3-yne (1: R¹=Me, R²=Me, n=2)

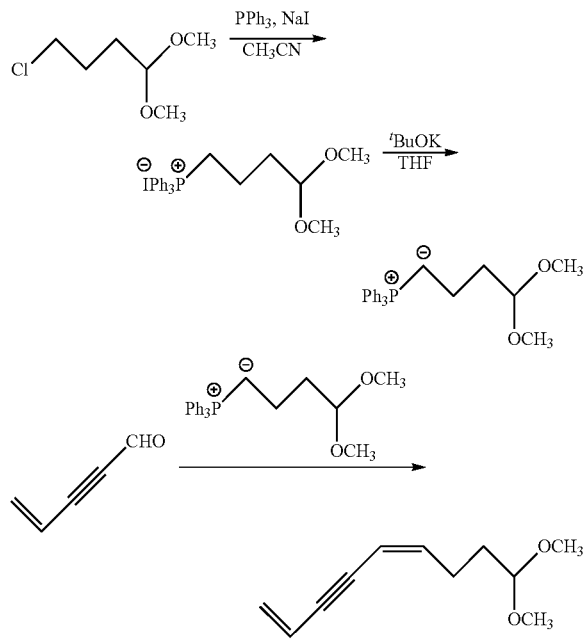

9-Chloro-1,1-dimethoxybutane (54.94 g, 0.36 mol), triphenylphosphine (PPh₃) (95.44 g, 0.36 mol), sodium iodide (54.41 g, 0.36 mol), potassium carbonate (2.90 g, 0.021 mol), and acetonitrile (192.45 g) woe placed in a reactor at room temperature and stirred at from 75 to 85° C. for 15 hours to obtain 4,4-dimethoxybutyltriphenylphosphonium iodide. Then, tetrahydrofuran (346.14 g) was added dropwise to the reactor at 30 to 40° C. After the completion of the dropwise addition, the reaction mixture was cooled to −5 to 10° C. Next, potassium t-butoxide (38.71 g, 0.35 mol) was added and stirred for 1 hour to obtain triphenylphosphonium 4,4-dimethoxybutylide (4: Ar=Ph; R¹=Me, R²=Me).

Next 4-penten-2-ynal (3) (16.96 g, 0.21 mol), which had been prepared as in Example 7 and purified, in a mixed liquid of toluene (361.59 g) and tetrahydrofuran (109.22 g) was added dropwise to the reactor at from −5 to 5° C. After the completion of the dropwise addition, the reaction mixture was stirred at from 20 to 30° C. for 2 hours. Next a solution of sodium chloride (45.47 g) in water (454.65 g) was added to the reaction mixture, followed by phase separation and removal of the aqueous phase to obtain the organic phase. Then, the organic phase was concentrated at a reduced pressure, and the residue was subjected to distillation at a reduced pressure (95.2 to 107.1° C./8.0 mmHg (1.07 kPa)) to obtain 9,9-dimethoxy-1,5-nonadien-3-yne (1: R¹=Me, R²=Me; n=2) (37.85 g, 0.16 mol, purity: 74.11%, E/Z=23/77) in a yield of 73.56%.

The following is the spectrum data of 9,9-dimethoxy-1,5-nonadien-3-yne (1: R¹=Me, R²=Me; n=2) thus produced.

[Nuclear magnetic resonance spectrum]¹H-NMR (500 MHz, CDCl₃): δ 1.68-1.74 (2H, q-like), 237 (2a ddt J=1.1 Hz, 8.0 Hz, 8.0 Hz), 3.32 (6H, s), 4.36 (1H, t, J=5.7 Hz), 5.45 (1H, dd, J=2.3 Hz, 11.1 Hz), 5.56-5.61 (1H, m), 5.61 (1H, dd, J=2.3 Hz, 172 Hz), 5.88-5.97 (2a m); ¹³C-NMR (125 MHz, CDCl₃): δ 25.56, 31.63, 52.80, 86.62, 92.57, 103.97, 109.56, 117.31, 126.21, 142.88.

[Mass spectrum] EI-Mass spectrum (70 eV): m/z 180 (M⁺), 165, 147, 133, 117, 105, 91, 75, 65.

[Infrared absorption spectrum] (NaCl): νmax 2951, 2830, 1598, 1445, 1415, 1385, 1365, 1178, 1159, 1127, 1066, 972, 921, 742.

Example 13

Preparation of 4,8-nonadien-6-ynal (2: n=2)

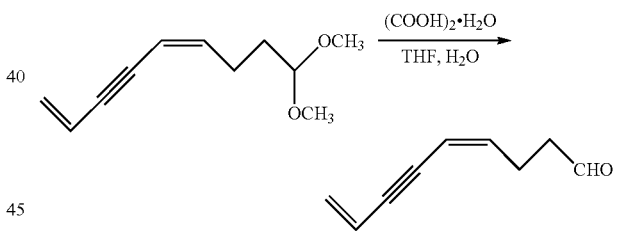

The product obtained in Example 1Z 9,9-dimethoxy-1,5-nonadien-3-yne (1: R¹=Me, R²=Me; n=2) (33.80 g, 0.14 mol purity: 74.11%, E/Z=23/77), oxalic acid dihydrate (52.57 g, 0.42 mol), tetrahydrofuran (139.00 g), and pure water (139.00 g) were placed in a reactor at room temperature and stirred at from 60 to 65° C. for 3.5 hours. Then, tire reaction mixture was coded to 50° C., and hexane (40.88 g) was added, and the reaction mixture was stirred for 30 minutes. After completion of the stirring, the reaction mixture was allowed to stand for phase separation, followed by removal of the aqueous phase to obtain the organic phase. Then, the organic phase was concentrated at a reduced pressure and tire residue was subjected to distillation at a reduced pressure (70.0 to 97.1° C./11.0 mmHg (1.47 kPa)) to obtain 4,8-nonadien-6-ynal (2: n=2) (16.60 g, 0.12 mol, purity: 95.85%, E/Z=23/77) in a yield of 85.33%.

The following is tire spectrum data of 4,8-nonadien-6-ynal (2: n=2) tints produced.

[Nuclear magnetic resonance spectrum]¹H-NMR (500 MHz, CDCl₃): δ 2.53-2.66 (4H, m), 5.47 (1H, dd, J=1.9 Hz, 11.2 Hz), 5.62 (1H, dd, J=1.9 Hz, 17.6 Hz), 5.60-5.65 (1H, m), 5.87-5.97 (2H, m), 9.77 (1H, t, J=1.5 Hz); $^{13}$C-NMR (125 MHz, CDCl$_3$): δ 22.95, 42.79, 86.11, 93.29, 110.54, 117.08, 126.61, 140.97, 201.39,

[Mass spectrum] EI-Mass spectrum (70 eV): m/z 133 (M$^+$-1), 115, 105, 91, 78, 65, 51,

[Infrared absorption spectrum] (NaCl): vmax 2895, 2826, 2726, 1724, 1591, 1413, 1390, 1159, 973, 922, 738, Example 14

Preparation of 14,14-dimethoxy-1,5-tetradecadien-3-yne (1: R$^1$=Me, R$^2$=Me; n=7)

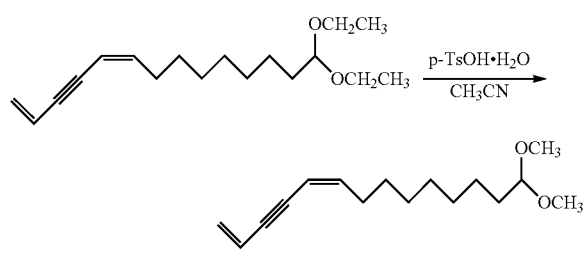

14,14-Diethoxy-1,5-tetradecadien-3-yne (1: R$^1$=Et, R$^2$=Et; n=7) prepared as in Example 8 and purified (4.66 g, 0.016 mol, purity: 95.79%, E/Z=1/99), p-toluene sulfonate monohydrate (0.031 g, 0.00016 mol), and methanol (154.08 g) were placed in a reactor at room temperature and stirred at from 60 to 65° C. for 2 hours. Then, the reaction mixture was coded to 50° C., to winch an aqueous 25% by mass solution of sodium hydroxide (1.0 g), water (80.00 g) and hexane (80.00 g) were then added and stirred for 30 minutes. Subsequently, an aqueous 25% by mass solution of sodium hydroxide (1.0 g), and water (80.00 g) were added to the reaction mixture in this order. The reaction mixture was allowed to stand for phase separation, followed by removal of the aqueous phase to obtain tire organic phase. Then, tire organic phase was concentrated at a reduced pressure and the residue was purified by silica gel chromatography (hexane/ethyl acetate=90/1 to 50/1 in V/V) to obtain 14,14-dimethoxy-1,5-tetradecadien-3-yne (1: R$^1$=Me, R$^2$=Me; n=7) (3.67 g, 0.015 mol purity: 99.54%, E/Z=1/99) in a yield of 90.97%.

The following is the spectrum data of 14,14-dimethoxy-1,5-tetradecadien-3-yne (1: R$^1$=Me, R$^2$=Me; n=7) thus produced.

[Nuclear magnetic resonance spectrum] $^1$H-NMR (500 MHz, CDCl$_3$): δ 1.25-1.36 (8H, br.s), 1.36-1.44 (2H, quint-like), 1.54-1.61 (2H, q-like), 2.30 (2H, ddt, J=1.1 Hz, 7.4 Hz, 7.4 Hz), 3.30 (6H, s), 4.34 (1H, t, J=5.7 Hz), 5.44 (1H, J=1.9 Hz, 11.3 Hz), 5.53-5.58 (1H, m) 5.60 (1H, dd, J=1.9 Hz, 17.6 Hz), 5.87-5.97. (2H, m); $^{13}$C-NMR (125 MHz, CDCl$_3$): δ 24.54, 28.74, 28.99, 29.29, 29.36, 30.22, 32.44, 52.52, 87.02, 92.13, 104.51, 108.81, 117.39, 125.99, 144.33,

[Mass spectrum] EI-Mass spectrum (70 eV): m/z 250 (M+), 219, 187, 145, 131, 117, 104, 91, 75, 65,

[Infrared absorption spectrum] (NaCl): vmax 2928, 2855, 2829, 1599, 1464, 1414, 1386, 1364, 1192, 1127, 1055, 969, 915, 738, Example 15

Preparation of 9,9-diethoxy-1,5-nonadien-3-yne (1: R$^1$=Et, R$^2$=Et; n=2)

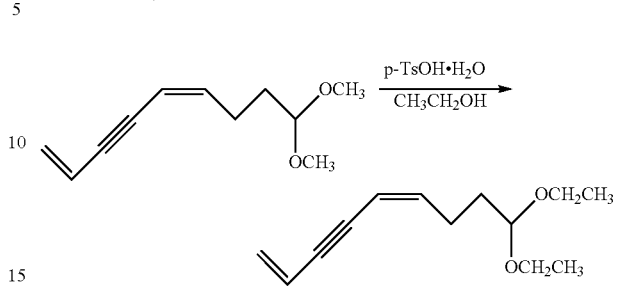

9,9-Dimethoxy-1,5-nonadien-3-yne (1: R$^1$=Me, R$^2$=Me) prepared as in Example 12 and purified (1.45 g, 0.0080 mol, purity: 99.85%, E/Z=0/100), p-toluene sulfonate monohydrate (0.016 g. 0.000084 mol), and ethanol (111.02 g, 2.41 mol) were placed in a reactor at room temperature and stirred at from 60 to 65° C. for 2 hours. Then, tire reaction mixture was coded to 50° C., to which an aqueous 25% by mass solution of sodium hydroxide (1.0 g), water (80.00 g) and hexane (80.00 g) were then added and stirred for 30 minutes. Subsequently, an aqueous 25% by mass solution of sodium hydroxide (1.0 g), and water (80.00 g) were added to tire reaction mixture in this order. The reaction mixture was allowed to stand for phase separation, followed by removal of the aqueous phase to obtain the organic phase. Then, foe organic phase was concentrated at a reduced pressure and the residue was purified by silica gel chromatography (hexane/ethyl acetate=90/1 in V/V) to obtain 9,9-diethoxy-1,5-nonadien-3-yne (1: R$^1$=Et, R$^2$=Et; n=2) (135 g, 0.0065 mol, purity: 99.61%, E/Z=0/100) in a yield of 80.52%.

The following is the spectrum data of 9,9-diethoxy-1,5-nonadien-3-yne (1: R$^1$=Et, R$^2$=Et; n=2) thus produced.

[Nuclear magnetic resonance spectrum] $^1$H-NMR (500 MHz, CDCl$_3$): δ 1.20 (6H, t, J=7.1 Hz), 1.72 (2H, ddt, J=1.5 Hz, 6.9 Hz, 6.9 Hz), 2.39 (2H, ddt J=1.2 Hz, 7.6 Hz, 7.6 Hz): 3.49 (2H, dq, J=6.9 Hz, 7.9 Hz), 3.65 (2H, dq, J=6.9 Hz, 7.8 Hz), 4.48 (1H, t, J=5.8 Hz). 5.44 (1H, dd, J=1.9 Hz, 11.1 Hz), 5.55-5.60 (1H, m), 5.60 (1H, dd, J=1.9 Hz, 17.6 Hz), 5.89-5.97 (2H, m); $^{13}$C-NMR (125 MHz, CDCl$_3$): δ 15.31, 25.76, 32.70, 61.14, 86.71, 92.49, 102.31, 109.40, 117.31, 126.13, 143.16.

[Mass spectrum] H-Mass spectrum (70 eV): m/z 207<MM), 179, 162, 133, 117, 105, 91, 75, 64.

[Mated absorption spectrum] (NaCl): vmax 2975, 2929, 2879, 1599, 1444, 1414, 1373, 1347, 1160, 1130, 1063, 972, 918, 741.

Example 16

Preparation of 9,9-dimethoxy-1,5-nonadien-3-yne (1: R$^1$=Me, R$^2$=Me; n=2)

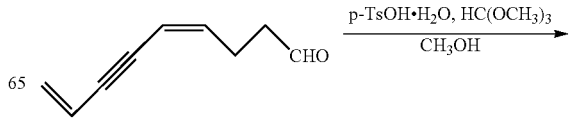

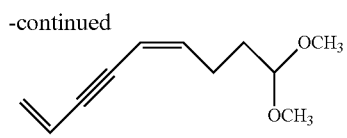

4,8-Nonadien-6-ynal (2: n=2) prepared as in Example 13 and purified (3.26 g, 0.023 mol, purity: 94.20%, E/Z=0/100), p-toluene sulfonate monohydrate (0.0031 g, 0.000016 mol), methyl orthoformate (3.62 g, 0.034 mol), and methanol (34.08 g) were place in a reactor at room temperature and stirred at from 20 to 30° C. for 2 hours. Then, water (34.00 g) and hexane (34.00 g) were added and stirred for 30 minutes. Water (34.00 g) was added to the reaction mixture. The reaction mixture was allowed to stand for phase separation, followed by removal of the aqueous phase to obtain the organic phase. Then, the organic phase was concentrated at a reduced pressure and the residue was purified by silica gel chromatography (hexane/ethyl acetate=90/1 mV/V) to obtain 9,9-dimethoxy-1,5-nonadien-3-yne (1: $R^1$=Me, $R^2$=Me; n=2) (3.51 g, 0.019 mol, purity: 99.85%, E/Z=0/100) in a yield of 84.93%.

The spectra data of 9,9-dimethoxy-1,5-nonadien-3-yne (1: $R^1$=Me, $R^2$=Me; n=2) thus obtained were same as those in Example 12.

The invention claimed is:

1. A process for preparing a dienynal compound of the following general formula (2):

$$CH_2=CHC\equiv CCH=CH(CH_2)_nCHO \qquad (2)$$

wherein n represents an integer of 0 to 11,
the process comprising a step of hydrolyzing a dialkoxyalkadienyne compound of the following general formula (1):

$$CH_2=CHC\equiv CCH=CH(CH_2)_nCH(OR^1)(OR^2) \qquad (1)$$

wherein $R^1$ and $R^2$ represent, independently of each other, a monovalent hydrocarbon group having 1 to 15 carbon atoms, or $R^1$ and $R^2$ may be bonded to each other to form a divalent hydrocarbon group, $R^1$-$R^2$, having from 2 to 10 carbon atoms, and n represents an integer of 0 to 11,
to obtain the dienynal compound (2).

2. The process for preparing foe dienynal compound (2) according to claim 1, further comprising a step of
subjecting 4-penten-2-ynal of the following formula (3):

$$CH_2=CHC\equiv CCHO \qquad (3)$$

to a Wittig reaction with a triarylphosphonium dialkoxyalkylide compound of the following general formula (4):

$$Ar_3P^+C^-H(CH_2)_nCH(OR^1)(OR^2) \qquad (4)$$

wherein Ar may be same as or different from each other and represents an aryl group, $R^1$ and $R^2$ are as defined above, and n represents an integer of 0 to 11,
to obtain foe dialkoxyalkadienyne compound (1).

3. The process for preparing the dienynal compound (2) according to claim 2, further comprising a step of
hydrolyzing a 5,5-dialkoxy-1-penten-3-yne compound of the following general formula (5):

$$CH_2=CHC\equiv CCH(OR^3)(OR^4) \qquad (5)$$

wherein $R^3$ and $R^4$ represent, independent of each other, a monovalent hydrocarbon group having 1 to 15 carbon atoms, or $R^3$ and $R^4$ may be bonded to each other to form a divalent hydrocarbon group, $R^3$-$R^4$, having from 2 to 10 carbon atoms, to obtain 4-penten-2-ynal (3).

4. The process for preparing the dienynal compound (2) according to claim 3, further comprising a step of
eliminating a leaving group in a 2-ynal acetal compound of the following general formula (6):

$$Z(CH_2)_2C\equiv CCH(OR^3)(OR^4) \qquad (6)$$

wherein $R^3$ and $R^4$ are as defined above, and Z represents a leaving group selected from the group consisting of an alkoxy group having 1 to 12 carbon atoms, an acyloxy group having 1 to 10 carbon atoms, a silyloxy group having 3 to 20 carbon atoms, an alkanesulfonyloxy group having 1 to 10 carbon atoms, an arenesulfonyloxy group having 6 to 20 carbon atoms, and a halogen atom, in the presence of a base
to obtain the 5,5-dialkoxy-1-penten-3-yne compound (5).

5. A process for preparing a dialkoxyalkadienyne compound of the following general formula (1):

$$CH_2=CHC\equiv CCH=CH(CH_2)_nCH(OR^1)(OR^2) \qquad (1)$$

wherein $R^1$ and $R^2$ represent independently of each other, a monovalent hydrocarbon group having 1 to 15 carbon atoms, or $R^1$ and $R^2$ may be bonded to each other to form a divalent hydrocarbon group, $R^1$-$R^2$, having from 2 to 10 carbon atoms, and n represents an integer of 0 to 11,
the process comprising a step of
subjecting 4-penten-2-ynal of the following formula (3):

$$CH_2=CHC\equiv CCHO \qquad (3)$$

to a Wittig reaction with a triarylphosphonium dialkoxyalkylide compound of the following general formula (4):

$$Ar_3P^+C^-H(CH_2)_nCH(OR^1)(OR^2) \qquad (4)$$

wherein Ar may be same as or different from each other and represents an aryl group, and $R^1$, $R^2$ and n are as defined above,
to obtain the dialkoxyalkadienyne compound (1).

6. A dialkoxyalkadienyne compound of the following general formula (1)

$$CH_2=CHC\equiv CCH=CH(CH_2)_nCH(OR^1)(OR^2) \qquad (1)$$

wherein $R^1$ and $R^2$ represent, independently of each other, a monovalent hydrocarbon group having 1 to 15 carbon atoms, or $R^1$ and $R^2$ may be bonded to each other to form a divalent hydrocarbon group, $R^1$-$R^2$, having from 2 to 10 carbon atoms, and n represents an integer of 0 to 11.

7. The process according to claim 1, wherein $R^1$ and $R^2$ represent, independently of each other, a monovalent hydrocarbon group having 1 to 8 carbon atoms.

8. The process according to claim 1, wherein $R^1$ and $R^2$ represent, independently of each other, a monovalent hydrocarbon group having 1 to 4 carbon atoms.

9. The process according to claim 1, wherein $R^1$ and $R^2$ are bonded to each other to form a divalent hydrocarbon group, $R^1$-$R^2$, having from 2 to 10 carbon atoms, and n represents an integer of 0 to 11.

10. The process according to claim 3, wherein $R^1$ and $R^2$ represent, independently of each other, a monovalent hydrocarbon group having 1 to 8 carbon atoms.

11. The process according to claim 3, wherein $R^1$ and $R^2$ represent, independently of each other, a monovalent hydrocarbon group having 1 to 4 carbon atoms.

12. The process according to claim 3, wherein $R^1$ and $R^2$ represent, independently of each other, to form a divalent hydrocarbon group, $R^1$-$R^2$, having from 2 to 10 carbon atoms, and n represents an integer of 0 to 11.

13. The process according to claim 5, wherein $R^1$ and $R^2$ represent, independently of each other, a monovalent hydrocarbon group having 1 to 8 carbon atoms.

14. The process according to claim 5, wherein $R^1$ and $R^2$ represent, independently of each other, a monovalent hydrocarbon group having 1 to 4 carbon atoms.

15. The process according to claim 5, wherein $R^1$ and $R^2$ are bonded to each other to form a divalent hydrocarbon group, $R^1$-$R^2$, having from 2 to 10 carbon atoms, and n represents an integer of 0 to 11.

16. The process according to claim 6, wherein $R^1$ and $R^2$ represent, independently of each other, a monovalent hydrocarbon group having 1 to 8 carbon atoms.

17. The process according to claim 6, wherein $R^1$ and $R^2$ represent, independently of each other, a monovalent hydrocarbon group having 1 to 4 carbon atoms.

18. The process according to claim 6, wherein $R^1$ and $R^2$ are bonded to each other to form a divalent hydrocarbon group, $R^1$-$R^2$, having from 2 to 10 carbon atoms, and n represents an integer of 0 to 11.

\* \* \* \* \*

UNITED STATES PATENT AND TRADEMARK OFFICE
CERTIFICATE OF CORRECTION

| | |
|---|---|
| PATENT NO. | : 11,148,989 B2 |
| APPLICATION NO. | : 17/010241 |
| DATED | : October 19, 2021 |
| INVENTOR(S) | : Miyake et al. |

It is certified that error appears in the above-identified patent and that said Letters Patent is hereby corrected as shown below:

In the Specification

Column 4, Line 50: Please correct "(n=1)" to read -- (n=11) --

Column 5, Line 17: Please correct "(n=M)" to read -- (n=4) --

Column 5, Line 29: Please correct "-diheptoxy-" to read -- -dipentoxy- --

Column 6, Line 38: Please correct "CH(OR$^1$(OR$^2$)" to read -- CH(OR$^1$)(OR$^2$) --

Column 6, Line 55: Please correct "mere" to read -- more --

Column 8, Line 63: Please correct "confound" to read -- compound --

Column 11, Line 1: Please correct "3.000 g" to read -- 3,000 g --

Column 12, Line 17: Please correct "22-" to read -- 2,2- --

Column 13, Line 40: Please correct "XCH(CH$_2$)$_7$CH(OR$^1$(OR$^2$)" to read
-- XCH(CH$_2$)$_7$CH(OR$^1$)(OR$^2$) --

Column 13, Line 62: Please correct "-dipropxynonane" to read -- -dipropoxynonane --

Column 13, Line 64: Please correct "-dipentoxynonane" to read -- -diheptoxynonane --

Column 14, Line 1: Please correct "dipropxynonane" to read -- dipropoxynonane --

Column 14, Line 3: Please correct "-dipentoxynonane" to read -- -diheptoxynonane --

Column 14, Line 6: Please correct "-dipropxynonane" to read -- -dipropoxynonane --

Signed and Sealed this
Fifth Day of April, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,148,989 B2

Column 14, Line 8: Please correct "-dipentoxynonane" to read -- -diheptoxynonane --

Column 14, Line 39: Please correct "tire" to read -- the --

Column 17, Line 15: Please correct "CH(OR$^1$(OR$^2$)" to read -- CH(OR$^1$)(OR$^2$) --

Column 17, Line 33: Please correct "foe" to read -- the --

Column 17, Line 41: Please correct "foe" to read -- the --

Column 17, Line 53: Please correct "ail" to read -- an --

Column 19, Line 3: Please correct "foe" to read -- the --

Column 19, Line 11: Please correct "CH(OR$^1$(OR$^2$)" to read -- CH(OR$^1$)(OR$^2$) --

Column 19, Line 32: Please correct "foe" to read -- the --

Column 20, Line 50: Please correct "-1,3-ynal" to read -- -13-ynal --

Column 20, Line 52: Please correct "-1,3-ynal" to read -- -13-ynal --

Column 21, Lines 15-19:
Please correct "Yield (%) = {[(weight of *a* product obtained *by a* reaction × % *GC*) / molecular weight of *a* product] ÷ [(weight of *a* starting material in *a* reaction × % *GC*) / molecular weight of *a* starting material]} × 100" to read -- Yield (%) = {[(weight of a product obtained by a reaction × % GC) / molecular weight of a product] ÷ [(weight of a starting material in a reaction × % GC) / molecular weight of a starting material]} × 100 --

Column 21, Line 39: Please correct "40239 g" to read -- 402.39 g --

Column 21, Line 56: Please correct "tins" to read -- thus --

Column 21, Line 59: Please correct "1H, J=1.6" to read -- 1H, d, J=1.6 --

Column 21, Line 62: Please correct "125 MHZ" to read -- 125 MHz --

Column 22, Line 10: Please correct "THF" to read -- DMF --

Column 22, Lines 20-21: Please correct "N,N-dimethylfomamide" to read -- N,N-dimethylformamide --

Column 22, Line 59: Please correct "731 g" to read -- 7.31 g --

Column 22, Line 63: Please correct "mol purity" to read -- mol, purity --

CERTIFICATE OF CORRECTION (continued)
U.S. Pat. No. 11,148,989 B2

Column 22, Line 65: Please correct "flic" to read -- the --

Column 23, Line 5: Please correct "513" to read -- 51.3 --

Column 23, Line 7: Please correct "3621 g" to read -- 36.21 g --

Column 23, Line 9: Please correct "plectra" to read -- spectra --

Column 23, Line 38: Please correct "021 mol" to read -- 0.21 mol --

Column 23, Line 42: Please correct "Z=CH$_3$C(=O) —C))" to read -- Z=CH$_3$C(=O)—O) --

Column 23, Line 51: Please correct "692" to read -- 69.2 --

Column 23, Line 54: Please correct "foe" to read -- the --

Column 23, Line 58: Please correct "1H, J=1.1 Hz" to read -- 1H, d, J=1.1 Hz --

Column 23, Line 59: Please correct "J=23 Hz" to read -- J=2.3 Hz --

Column 23, Line 62: Please correct "H-Mass" to read -- EI-Mass --

Column 23, Line 63: Please correct "(MM)" to read -- (M$^+$-1) --

Column 24, Line 21: Please correct "traced" to read -- placed --

Column 24, Line 32: Please correct "692" to read -- 69.2 --

Column 25, Line 30: Please correct "(020 g)" to read -- (0.20 g) --

Column 25, Line 31: Please correct "stoned" to read -- stirred --

Column 25, Line 36: Please correct "27231 g" to read -- 272.31 g --

Column 25, Line 49: Please correct "J=172" to read -- J=17.2 --

Column 25, Line 51: Please correct "23 Hz" to read -- 2.3 Hz --

Column 25, Line 54: Please correct "61.52" to read -- 61, 52 --

Column 25, Line 55: Please correct "Mated" to read -- Infrared --

Column 26, Line 33: Please correct "024 mol" to read -- 0.24 mol --

Column 26, Line 36: Please correct "020 mol" to read -- 0.20 mol --

CERTIFICATE OF CORRECTION (continued)

Column 26, Line 59: Please correct "dq J=6.9 Hz" to read -- dq, J=6.9 Hz --

Column 27, Line 17: Please correct "mol purity" to read -- mol, purity --

Column 27, Line 18: Please correct "6921 g" to read -- 69.21 g --

Column 27, Line 29: Please correct "mol purity" to read -- mol, purity --

Column 27, Line 34: Please correct "hr. quint J=6.5" to read -- br. quint, J=6.5 --

Column 27, Line 35: Please correct "230" to read -- 2.30 --

Column 27, Line 37: Please correct "J=112 Hz, 19 Hz" to read -- J=11.2 Hz, 1.9 Hz --

Column 27, Line 42: Please correct "H-Mass" to read -- EI-Mass --

Column 28, Line 24: Please correct "020 mol" to read -- 0.20 mol --

Column 28, Line 30: Please correct "tire" to read -- the --

Column 28, Line 39: Please correct "ET" to read -- Et --

Column 28, Line 49: Please correct "Thai" to read -- Then --

Column 28, Line 53: Please correct "purity. 96.03%" to read -- purity: 96.03% --

Column 29, Line 25: Please correct "woe" to read -- were --

Column 29, Line 61: Please correct "woe" to read -- were --

Column 30, Line 21: Please correct "237 (2a ddt J=1.1" to read -- 2.37 (2H, ddt, J=1.1 --

Column 30, Line 24: Please correct "172 Hz" to read -- 17.2 Hz --

Column 30, Line 24: Please correct "(2a m)" to read -- (2H, m) --

Column 30, Line 48: Please correct "Example 1Z" to read -- Example 12, --

Column 30, Lines 49-50: Please correct "0.14 mol purity" to read -- 0.14 mol, purity --

Column 30, Line 53: Please correct "tire" to read -- the --

Column 30, Line 54: Please correct "coded" to read -- cooled --

Column 30, Line 64: Please correct "tire" to read -- the --

CERTIFICATE OF CORRECTION (continued)
U.S. Pat. No. 11,148,989 B2

Column 30, Line 65: Please correct "tints" to read -- thus --

Column 31, Line 35: Please correct "coded to 50° C., to winch" to read -- cooled to 50° C., to which --

Column 31, Line 43: Please correct "tire organic phase. Then, tire" to read -- the organic phase. Then, the --

Column 31, Line 48: Please correct "mol purity" to read -- mol, purity --

Column 31, Line 57: Please correct "1H, J=1.9" to read -- 1H, dd, J=1.9 --

Column 32, Line 21: Please correct "0.016 g." to read -- 0.016 g, --

Column 32, Line 23: Please correct "tire" to read -- the --

Column 32, Line 24: Please correct "coded" to read -- cooled --

Column 32, Line 29: Please correct "tire" to read -- the --

Column 32, Line 32: Please correct "foe" to read -- the --

Column 32, Line 35: Please correct "135" to read -- 1.35 --

Column 32, Line 49: Please correct "H-Mass" to read -- EI-Mass --

Column 32, Line 50: Please correct "207<MM)" to read -- 207($M^+$-1) --

Column 32, Line 52: Please correct "Mated" to read -- Infrared --

Column 33, Line 19: Please correct "mV/V" to read -- in V/V --

In the Claims

Column 33, Line 45, Claim 2: Please correct "foe" to read -- the --

Column 33, Line 58, Claim 2: Please correct "foe" to read -- the --